(12) United States Patent
Fadini et al.

(10) Patent No.: US 9,403,772 B2
(45) Date of Patent: *Aug. 2, 2016

(54) 4-(5-(2-(3,5-BIS(TRIFLUOROMETHYL) PHENYL)-N,2-DIMETHYLPROPANAMIDO)-4-(O-TOLYL)PYRIDIN-2-YL)-1-METHYL-1-((PHOSPHONOOXY)METHYL)PIPERAZIN-1-IUM AS A NEUROKININ RECEPTOR MODULATOR

(71) Applicant: HELSINN HEALTHCARE SA, Lugano/Pazzallo (CH)

(72) Inventors: Luca Fadini, Giubiasco (CH); Peter Manini, Giubiasco (CH); Claudio Pietra, Como (IT); Claudio Giuliano, Como (IT); Emanuela Lovati, Mendrisio (CH); Roberta Cannella, Varese (IT); Alessio Venturini, Varese (IT); Valentino J Stella, Lawrence, KS (US)

(73) Assignee: HELSINN HEALTHCARE SA, Lugano/Pazzallo (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/360,991

(22) PCT Filed: Nov. 28, 2012

(86) PCT No.: PCT/US2012/066778
§ 371 (c)(1),
(2) Date: May 28, 2014

(87) PCT Pub. No.: WO2013/082102
PCT Pub. Date: Jun. 6, 2013

(65) Prior Publication Data
US 2015/0011510 A1    Jan. 8, 2015

Related U.S. Application Data

(63) Continuation-in-part of application No. 13/478,361, filed on May 23, 2012, now Pat. No. 8,426,450.

(60) Provisional application No. 61/564,537, filed on Nov. 29, 2011.

(51) Int. Cl.
*C07D 401/04* (2006.01)
*C07D 213/74* (2006.01)
*C07D 213/89* (2006.01)
*C07F 9/06* (2006.01)
*C07D 213/72* (2006.01)
*C07D 213/76* (2006.01)

(52) U.S. Cl.
CPC ............ *C07D 213/89* (2013.01); *C07D 213/72* (2013.01); *C07D 213/74* (2013.01); *C07D 213/76* (2013.01); *C07D 401/04* (2013.01); *C07F 9/062* (2013.01)

(58) Field of Classification Search
CPC .............................. C07D 213/74; C07D 401/04
USPC .......................................... 544/360; 546/304
See application file for complete search history.

(56) References Cited

FOREIGN PATENT DOCUMENTS

| JP | 2001527083 A | 12/2001 |
|----|--------------|---------|
| JP | 2008534454 A | 8/2008 |
| WO | 2006/099968 A1 | 9/2006 |
| WO | 2011/061622 A1 | 5/2011 |

OTHER PUBLICATIONS

Japanese Office Action dated Aug. 25, 2015, which issued during prosecution Japanese Application No. 2014-210716, which corresponds to the present application.

*Primary Examiner* — Douglas M Willis
(74) *Attorney, Agent, or Firm* — Clark G. Sullivan

(57) ABSTRACT

Compounds and methods for the prevention and/or treatment of diseases which are pathophysiologically mediated by the neurokinin (NK$_1$) receptor, based on 4-(5-(2-(3,5-bis(trifluoromethyl)phenyl)-N,2-dimethylpropanamido)-4-(o-tolyl) 3yridine-2-yl)-1-methyl-1-((phosphonooxy)methyl)piperazin-1-ium and pharmaceutically acceptable salts thereof.

14 Claims, 1 Drawing Sheet

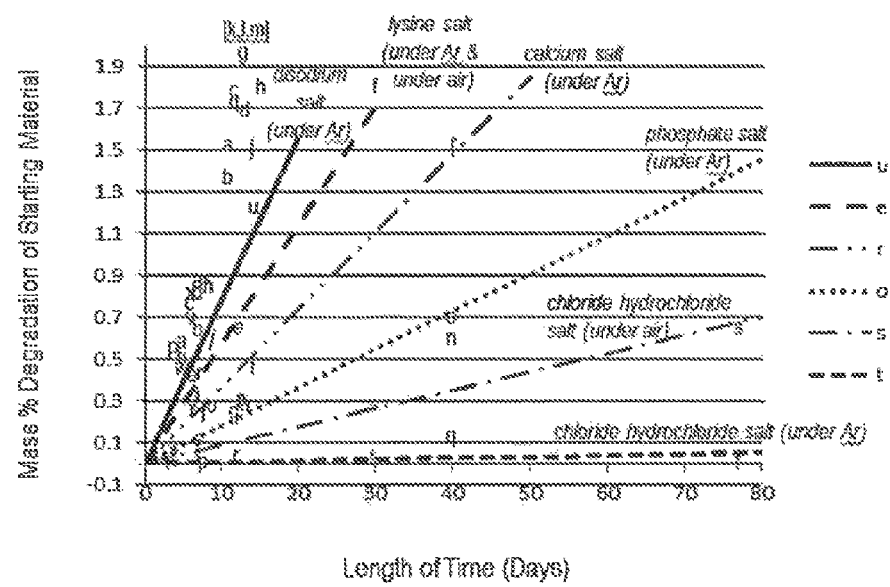
Degradation Behavior Over Time for Various Salts of 4-(5-(2-(3,5-bis(trifluoromethyl)phenyl)-N,2-dimethylpropanamido)-4-(o-tolyl)pyridin-2-yl)-1-methyl-1-((phos-phonooxy)methyl)piperazin-1-ium.

4-(5-(2-(3,5-BIS(TRIFLUOROMETHYL) PHENYL)-N,2-DIMETHYLPROPANAMIDO)-4-(O-TOLYL)PYRIDIN-2-YL)-1-METHYL-1-((PHOSPHONOOXY)METHYL)PIPERAZIN-1-IUM AS A NEUROKININ RECEPTOR MODULATOR

CROSS-REFERENCE TO RELATED APPLICATIONS

This application claims priority to U.S. Provisional Application 61/564,537, filed Nov. 29, 2011, and is a continuation in part of U.S. Non-provisional application Ser. No. 13/478,361, filed May 23, 2012.

BACKGROUND OF THE INVENTION

1. Field of the Invention

The present invention relates to novel 4-phenyl-pyridine compounds, and medical uses thereof, particularly in the prevention and/or treatment of medical conditions modulated by the neurokinin ($NK_1$) receptor.

2. Description of Related Art

Substance P is an 11-amino acid neuropeptide present reportedly involved in various pathological conditions including asthma, inflammation, pain, psoriasis, migraine, dyskinesia, cystitis, schizophrenia, emesis and anxiety, due to its localizations and functions. Substance P is an agonist for the NK1 receptor, and causes intracellular signal transduction through its interaction with the NK1 receptor.

The NK1 receptor has been reported to be implicated in various disorders and diseases, and various $NK_1$ antagonists have been developed for the purpose of treating or preventing such disorders and diseases. For example, Kramer et al. (*Science* 281 (5383), 1640-1645, 1988) reports clinical trials for $NK_1$ receptor antagonists in the treatment of anxiety, depression, psychosis, schizophrenia and emesis. Gesztesi et al. (*Anesthesiology* 93(4), 931-937, 2000) also reports the use of $NK_1$ receptor antagonists in the treatment of emesis U.S. Pat. No. 6,297,375 to Hoffmann-La Roche describes a class of 4-phenyl-pyridine compounds that are $NK_1$ antagonists which are useful for treating CNS disorders, such as depression, anxiety or emesis. Netupitant is a selective $NK_1$ receptor antagonist among these 4-phenyl-pyridine compounds, and is currently under clinical development in combination with palonosetron (a 5-$HT_3$ receptor antagonist) for the prevention of chemotherapy-induced-nausea and vomiting (CINV) by Helsinn Healthcare.

Mono-N-oxide derivatives of 4-phenyl-pyridine compounds are described in U.S. Pat. No. 6,747,026 to Hoffmann-La Roche. These N-oxide derivatives are reportedly intended to overcome limitations on the parent compounds that would otherwise limit their clinical usefulness, such as solubility or pharmacokinetic limitations. However, no physicochemical or biological data of the mono-N-oxide derivatives are reported in the '026 patent.

U.S. Pat. No. 5,985,856 to the University of Kansas describes water soluble N-phosphoryloxymethyl derivatives of secondary and tertiary amines, and the use of such derivatives to improve the solubility profiles of loxapine and cinnarizine. The '856 patent does not disclose how the N-phosphoryloxymethyl moiety would affect other critical attributes of the drug product, such as prodrug structure(s), prodrug stability, synthetic cost, and selectivity of the phosphorylomethylation protocol.

In view of the above, there is a need to find new derivatives of and methods for making 4-phenyl-pyridine compounds that are effective NK1 receptor antagonists, and that have enhanced physicochemical and/or biological properties.

SUMMARY

In view of the foregoing, the inventors have developed a novel class of 4-phenyl-pyridine derivatives that are particularly well-suited for antagonizing the $NK_1$ receptor and that have the following general formula (I):

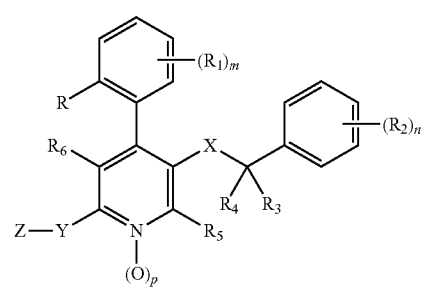

Formula (I)

and pharmaceutically acceptable salts or adducts thereof.

Compounds of formula (I), also known as 4-phenyl-pyridine derivatives, are particularly useful for preventing and/or treating diseases that are pathophysiologically related to the $NK_1$ receptor in a subject. Accordingly, in another embodiment the invention provides a method of treating a disease that is mediated by the NK1 receptor, comprising administering to said subject a therapeutically effective amount of a compound of formula (I), or a pharmaceutically acceptable salt or adduct thereof.

Also disclosed are pharmaceutical compositions for preventing and/or treating diseases which are pathophysiologically related to NK1 receptor in a subject, comprising a therapeutically effective amount of a compound of formula (I), or a pharmaceutically acceptable salt or adduct thereof, and one or more pharmaceutically acceptable excipients.

In one embodiment the invention is a compound of formula (I), or a pharmaceutically acceptable salt or adduct thereof,

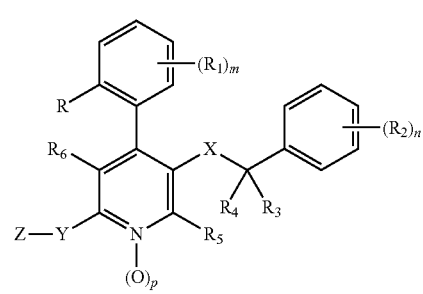

Formula (I)

wherein:

R is selected from the group consisting of hydrogen, hydroxy, hydroxyalkyl, amino, alkyl, alkenyl, cycloalkyl, halogen, alkoxyalkyl, —$OR^{101}$, —$NR^{101}R^{102}$, —$NR^{101}C(O)R^{102}$, —$C(O)R^{101}$, —$C(O)OR^{101}$, —$C(O)NR^{101}R^{102}$, -alkylN$R^{101}R^{102}$, —$S(O)_2R^{102}$, —$SR^{101}$, —$S(O)_2NR^{101}R^{102}$, aryl, arylalkyl, heterocycloalkyl, heterocycloalkylalkyl, heteroaryl and heteroarylalkyl, each optionally independently substituted with one or more independent $R^{103}$ substituents;

$R_1$ and $R_2$ are independently selected from the group consisting of hydrogen, hydroxy, hydroxyalkyl, amino, alkyl, alkenyl, cycloalkyl, halogen, alkoxyalkyl, —$OR^{101}$, —$NR^{101}R^{102}$, —$NR^{101}C(O)R^{102}$, —$C(O)R^{101}$, —$C(O)OR^{101}$, —$C(O)NR^{101}R^{102}$, -alkyl$NR^{101}R^{102}$, —$S(O)_2R^{102}$, —$SR^{101}$, —$S(O)_2NR^{101}R^{102}$, aryl, arylalkyl, heterocycloalkyl, heterocycloalkylalkyl, heteroaryl and heteroarylalkyl, each optionally independently substituted with one or more independent $R^{103}$ substituents; or $R_1$ together with the atoms and/or other substituent(s) on the same phenyl ring, form a fused or non-fused mono, bicyclic or tricyclic heterocyclic or carbocyclic ring which is optionally independently substituted with one or more $R^{103}$ substituents; or $R_2$ together with the atoms and/or other substituent(s) on the same phenyl ring, form a fused or non-fused mono, bicyclic or tricyclic heterocyclic or carbocyclic ring which is optionally independently substituted with one or more $R^{103}$ substituents;

$R_3$ and $R_4$ are independently selected from the group consisting of hydrogen, hydroxy, hydroxyalkyl, amino, alkyl, alkenyl, cycloalkyl, halogen, alkoxyalkyl, —$OR^{101}$, —$NR^{101}R^{102}$, —$NR^{101}C(O)R^{102}$, —$C(O)R^{101}$, —$C(O)OR^{101}$, —$C(O)NR^{101}R^{102}$, -alkyl$NR^{101}R^{102}$, —$S(O)_2R^{102}$, —$SR^{101}$, —$S(O)_2NR^{101}R^{102}$, aryl, arylalkyl, heterocycloalkyl, heterocycloalkylalkyl, heteroaryl and heteroarylalkyl, each optionally independently substituted with one or more independent $R^{103}$ substituents; or $R_3$ and $R_4$, together with the atoms connecting the same, form a fused or non-fused mono, bicyclic or tricyclic heterocyclic or carbocyclic ring which is optionally independently substituted with one or more $R^{103}$ substituents;

$R_5$ and $R_6$ are independently selected from the group consisting of hydrogen, hydroxy, hydroxyalkyl, amino, alkyl, alkenyl, cycloalkyl, halogen, alkoxyalkyl, —$OR^{101}$, —$NR^{101}R^{102}$, —$NR^{101}C(O)R^{102}$, —$C(O)R^{101}$, —$C(O)OR^{101}$, —$C(O)NR^{101}R^{102}$, -alkyl$NR^{101}R^{102}$, —$S(O)_2R^{102}$, —$SR^{101}$, —$S(O)_2NR^{101}R^{102}$, aryl, arylalkyl, heterocycloalkyl, heterocycloalkylalkyl, heteroaryl and heteroarylalkyl, each optionally independently substituted with one or more independent $R^{103}$ substituents;

X is selected from the group consisting of —$C(O)NR^{101}R^{102}$, -alkylO, -alkyl$NR^{101}R^{102}$, —$NR^{101}C(O)$ and —$NR^{101}$ alkyl, each optionally independently substituted with one or more independent $R^{103}$ substituents;

Y is selected from the group consisting of —$NR^{101}R^{102}$, —$NR^{101}$ alkylOH, —$NR^{101}S(O)_2$alkyl, —$NR^{101}S(O)_2$phenyl, —N=CH—$NR^{101}R^{102}$, heterocycloalkyl and heterocycloalkylalkyl, each optionally independently substituted with one or more independent $R^{103}$ substituents;

Z is a structural formula selected from the group consisting of:

—O⁻, (Ia)

—$OR^{100}$, (Ib)

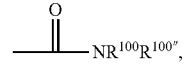
(Ic)

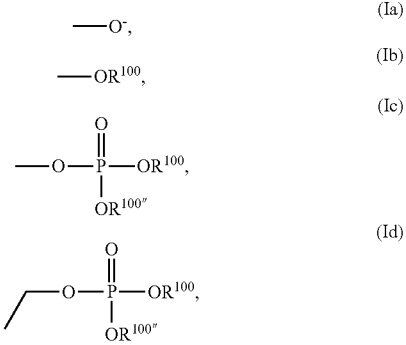
(Id)

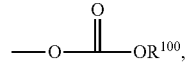
(Ie)

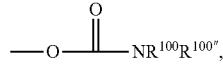
(If)

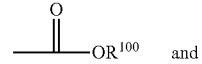
(Ig)

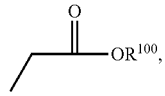
and (Ih)

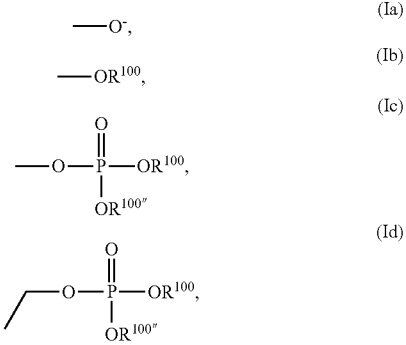
(Ii)

where formula (Ia) refers to an oxide;

$R^{100}$, $R^{100'''}$, $R^{101}$, $R^{102}$ and $R^{103}$ are each independently selected from the group consisting of hydrogen, cyano, —$NO_2$, —$OR^{104}$, oxide, hydroxy, amino, alkyl, alkenyl, cycloalkyl, halogen, alkoxy, alkoxyalkyl, aryl, arylalkyl, heterocycloalkyl, heterocycloalkylalkyl, heteroaryl, heteroarylalkyl, —$C(O)R^{104}$, —$C(O)OR^{104}$, —$C(O)NR^{104}R^{105}$, —$NR^{104}R^{105}$, —$NR^{104}S(O)_2R^{105}$, —$NR^{104}C(O)R^{105}$, —$S(O)_2R^{104}$, —$SR^{104}$ and —$S(O)_2NR^{104}R^{105}$, each optionally independently substituted with one or more independent $R^{103}$ substituents; or $R^{101}$, $R^{102}$, together with the atoms connecting the same, form a fused or non-fused mono, bicyclic or tricyclic heterocyclic or carbocyclic ring which is optionally independently substituted with one or more $R^{103}$ substituents; or $R^{10}$, $R^{100'''}$, together with the atoms connecting the same, form a fused or non-fused mono, bicyclic or tricyclic heterocyclic or carbocyclic ring which is optionally independently substituted with one or more $R^{103}$ substituents;

$R^{104}$ and $R^{105}$ are each independently selected from the group consisting of hydrogen, cyano, —$NO_2$, hydroxy, oxide, hydroxyalkyl, amino, alkyl, alkenyl, cycloalkyl, halogen, alkoxy, alkoxyalkyl, aryl, arylalkyl, heterocycloalkyl, heterocycloalkylalkyl, heteroaryl and heteroarylalkyl;

m is 0, 1, 2, 3, or 4;

n is 0, 1, 2, 3, 4 or 5;

p is 0 or 1; and with a proviso that if a non-pyridine N-Oxide (N⁻→O⁺) is present on the compound of Formula (I), then the total number of N-Oxide on the compound of Formula (I) is more than one.

In another embodiment the invention is the use of a therapeutically effective amount of a compound of formula (I) as defined above or a pharmaceutically acceptable salt or adduct thereof, in the manufacture of a medicament which is able to treat emesis, bladder dysfunction, depression or anxiety, in a patient in need thereof.

In an alternative embodiment the invention is a method of treating emesis, bladder dysfunction, depression or anxiety, in a patient in need thereof, comprising administering to said patient a therapeutically effective amount of a compound of formula (I) as defined above.

In still another embodiment the invention is a compound selected from the group consisting of:

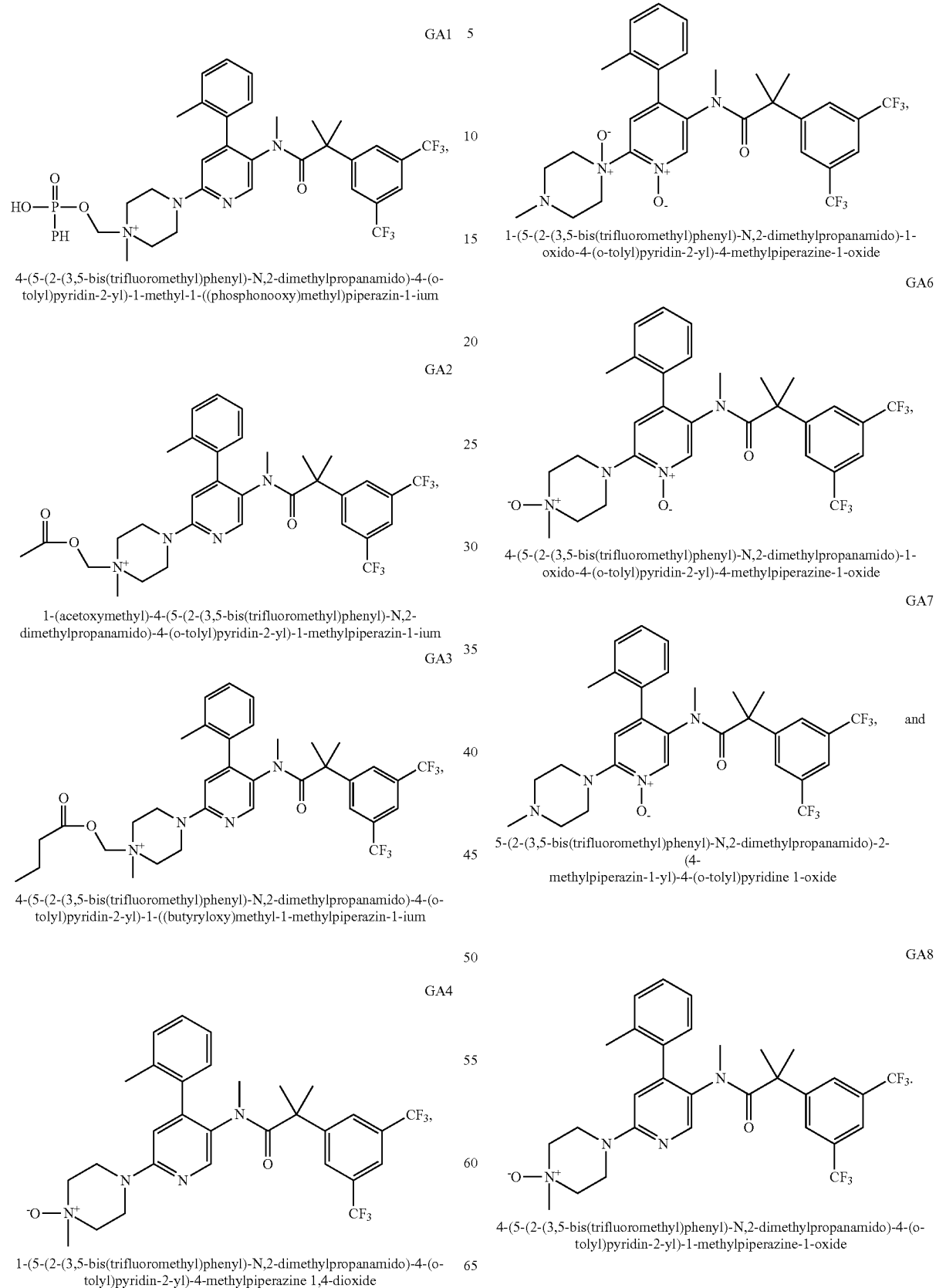

GA1

4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium

GA2

1-(acetoxymethyl)-4-(5-(2-(3,5-bis(trifluoromethyl)phenyl)-N,2-dimethylpropanamido)-4-(o-tolyl)pyridin-2-yl)-1-methylpiperazin-1-ium

GA3

4-(5-(2-(3,5-bis(trifluoromethyl)phenyl)-N,2-dimethylpropanamido)-4-(o-tolyl)pyridin-2-yl)-1-((butyryloxy)methyl-1-methylpiperazin-1-ium

GA4

1-(5-(2-(3,5-bis(trifluoromethyl)phenyl)-N,2-dimethylpropanamido)-4-(o-tolyl)pyridin-2-yl)-4-methylpiperazine 1,4-dioxide

GA5

1-(5-(2-(3,5-bis(trifluoromethyl)phenyl)-N,2-dimethylpropanamido)-1-oxido-4-(o-tolyl)pyridin-2-yl)-4-methylpiperazine-1-oxide

GA6

4-(5-(2-(3,5-bis(trifluoromethyl)phenyl)-N,2-dimethylpropanamido)-1-oxido-4-(o-tolyl)pyridin-2-yl)-4-methylpiperazine-1-oxide

GA7

5-(2-(3,5-bis(trifluoromethyl)phenyl)-N,2-dimethylpropanamido)-2-(4-methylpiperazin-1-yl)-4-(o-tolyl)pyridine 1-oxide and

GA8

4-(5-(2-(3,5-bis(trifluoromethyl)phenyl)-N,2-dimethylpropanamido)-4-(o-tolyl)pyridin-2-yl)-1-methylpiperazine-1-oxide or a pharmaceutically acceptable salt or adduct thereof.

In a further embodiment the invention is a compound of formula GA1,

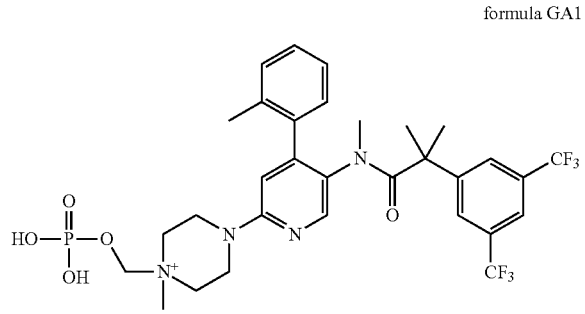

formula GA1

4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazine-1-ium or a pharmaceutically acceptable salt or adduct thereof.

BRIEF DESCRIPTION OF THE DRAWINGS

FIG. 1 reproduces stability data for various salts of 4-(5-(2-(3,5-bis(trifluoro-methyl)phenyl)-N,2-dimethylpropanamido)-4-(o-tolyl)pyridin-2-yl)-1-methyl-1-((phosphornooxy)methyl)piperazin-1-ium.

DETAILED DESCRIPTION

Before the present compounds, compositions, articles, devices, and/or methods are disclosed and described, it is to be understood that they are not limited to specific synthetic methods or specific treatment methods unless otherwise specified, or to particular reagents unless otherwise specified, as such may, of course, vary. It is also to be understood that the terminology used herein is for the purpose of describing particular embodiments only and is not intended to be limiting.

Materials

A. Compounds

Disclosed are compounds and pharmaceutically acceptable salts or adducts thereof represented by formula (I):

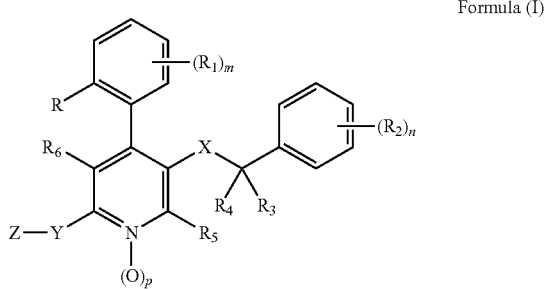

Formula (I)

wherein:
R is selected from the group consisting of hydrogen, hydroxy, hydroxyalkyl, amino, alkyl, alkenyl, cycloalkyl, halogen, alkoxy, alkoxyalkyl, —$OR^{101}$, —$NR^{101}R^{102}$, —$NR^{101}C(O)R^{102}$, —$C(O)R^{101}$, —$C(O)OR^{101}$, —$C(O)NR^{101}R^{102}$, -alkyl$NR^{101}R^{102}$, —$S(O)2R^{102}$, —$SR^{101}$, —$S(O)_2NR^{101}R^{102}$, aryl, arylalkyl, heterocycloalkyl, heterocycloalkylalkyl, heteroaryl and heteroarylalkyl, each optionally independently substituted with one or more independent $R^{103}$ substituents;

$R_1$ and $R_2$ are independently selected from the group consisting of hydrogen, hydroxy, hydroxyalkyl, amino, alkyl, alkenyl, cycloalkyl, halogen, alkoxy, alkoxyalkyl, —$OR^{101}$, —$NR^{101}R^{102}$, —$NR^{101}C(O)R^{102}$, —$C(O)R^{101}$, —$C(O)OR^{101}$, —$C(O)NR^{101}R^{102}$, -alkyl$NR^{101}R^{102}$, —$S(O)_2R^{102}$, —$SR^{101}$, —$S(O)_2NR^{101}R^{102}$, aryl, arylalkyl, heterocycloalkyl, heterocycloalkylalkyl, heteroaryl and heteroarylalkyl, each optionally independently substituted with one or more independent $R^{103}$ substituents; or $R_1$ together with the atoms and/or other substituent(s) on the same phenyl ring form a fused or non-fused mono, bicyclic or tricyclic heterocyclic or carbocyclic ring which is optionally independently substituted with one or more $R^{103}$ substituents; or $R_2$ together with the atoms and/or other substituent(s) on the same phenyl ring form a fused or non-fused mono, bicyclic or tricyclic heterocyclic or carbocyclic ring which is optionally independently substituted with one or more $R^{103}$ substituents;

$R_3$ and $R_4$ are independently selected from the group consisting of hydrogen, hydroxy, hydroxyalkyl, amino, alkyl, alkenyl, cycloalkyl, halogen, alkoxy, alkoxyalkyl, —$OR^{101}$, —$NR^{101}R^{102}$, —$NR^{101}C(O)R^{102}$, —$C(O)R^{101}$, —$C(O)OR^{101}$, —$C(O)NR^{101}R^{102}$, -alkyl$NR^{101}R^{102}$, —$S(O)_2R^{102}$, —$SR^{101}$, —$S(O)_2NR^{101}R^{102}$, aryl, arylalkyl, heterocycloalkyl, heterocycloalkylalkyl, heteroaryl and heteroarylalkyl, each optionally independently substituted with one or more independent $R^{103}$ substituents; or $R_3$ and $R_4$, together with the atoms connecting the same form a fused or non-fused mono, bicyclic or tricyclic heterocyclic or carbocyclic ring which is optionally independently substituted with one or more $R^{103}$ substituents;

$R_5$ and $R_6$ are independently selected from the group consisting of hydrogen, hydroxy, hydroxyalkyl, amino, alkyl, alkenyl, cycloalkyl, halogen, alkoxy, alkoxyalkyl, —$OR^{101}$, —$NR^{101}R^{102}$, —$NR^{101}C(O)R^{102}$, —$C(O)R^{101}$, —$C(O)OR^{101}$, —$C(O)NR^{101}R^{102}$, -alkyl$NR^{101}R^{102}$, —$S(O)_2R^{102}$, —$SR^{101}$, —$S(O)_2NR^{101}R^{102}$, aryl, arylalkyl, heterocycloalkyl, heterocycloalkylalkyl, heteroaryl and heteroarylalkyl, each optionally independently substituted with one or more independent $R^{103}$ substituents;

X is selected from the group consisting of —$C(O)NR^{101}R^{102}$, -alkylO, -alkyl$NR^{101}R^{102}$, —$NR^{101}C(O)$ and —$NR^{101}$ alkyl, each optionally independently substituted with one or more independent $R^{103}$ substituents;

Y is selected from the group consisting of —$NR^{101}R^{102}$, —$NR^{101}$alkylOH, —$NR^{101}S(O)_2$alkyl, —$NR^{101}S(O)_2$phenyl, —N=CH—$NR^{101}R^{102}$, heterocycloalkyl and heterocycloalkylalkyl, each optionally independently substituted with one or more independent $R^{103}$ substituents;

Z is a structural formula selected from the group consisting of:

  (Ia)

  (Ib)

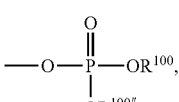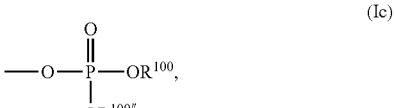  (Ic)

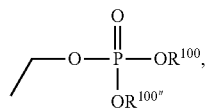
(Id)

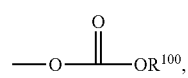
(Ie)

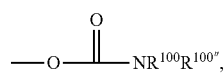
(If)

(Ig)

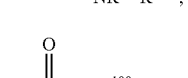
(Ih)

and

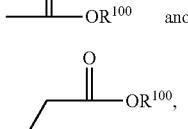
(Ii)

where formula (Ia) refers to an oxide;

$R^{101}$, $R^{101\prime\prime}$, $R^{101\prime}$, $R^{102}$ and $R^{103}$ are each independently selected from the group consisting of hydrogen, cyano, —$NO_2$, —$OR^{104}$, oxide, hydroxy, amino, alkyl, alkenyl, cycloalkyl, halogen, alkoxy, alkoxyalkyl, aryl, arylalkyl, heterocycloalkyl, heterocycloalkylalkyl, heteroaryl, heteroarylalkyl, —$C(O)R^{104}$, —$C(O)OR^{104}$, —$C(O)NR^{104}R^{105}$, —$NR^{104}R^{105}$, —$NR^{104}S(O)_2R^{105}$, —$NR^{104}C(O)R^{105}$, —$S(O)_2R^{104}$, —$SR^{104}$ and —$S(O)_2NR^{104}R^{105}$, each optionally independently substituted with one or more independent $R^{103}$ substituents; or $R^{101}$, $R^{102}$, together with the atoms connecting the same, form a fused or non-fused mono, bicyclic or tricyclic heterocyclic or carbocyclic ring which is optionally independently substituted with one or more $R^{103}$ substituents; or $R^{100}$, $R^{100\prime\prime}$, together with the atoms connecting the same, form a fused or non-fused mono, bicyclic or tricyclic heterocyclic or carbocyclic ring which is optionally independently substituted with one or more $R^{103}$ substituents;

$R^{104}$ and $R^{105}$ are each independently selected from the group consisting of hydrogen, cyano, —$NO_2$, hydroxy, oxide, hydroxyalkyl, amino, alkyl, alkenyl, cycloalkyl, halogen, alkoxy, alkoxyalkyl, aryl, arylalkyl, heterocycloalkyl, heterocycloalkylalkyl, heteroaryl and heteroarylalkyl;

m is from 0 to 4; n is from 0 to 5; p is from 0 to 1; and with a proviso that if a non-pyridine N-Oxide ($N^-\rightarrow O^+$) is present on the compound of Formula (I), then the total number of N-Oxide on the compound of Formula (I) is more than one. In another embodiment, the invention excludes all N-oxide forms.

In some forms, the compounds as presently disclosed are compounds of formula (I), or pharmaceutically acceptable salts or adducts thereof, wherein R, $R_1$, $R_2$, $R_3$, $R_4$, $R_5$ and $R_6$ are each independently selected from the group consisting of hydrogen, hydroxy, amino, alkyl, alkenyl, cycloalkyl, halogen, cyano, —$OR^{101}$ and $CF_3$.

In some other forms, the compounds as presently disclosed are compounds of formula (I), or pharmaceutically acceptable salts or adducts thereof, wherein X is —$NR^{101}C(O)$. In some other forms, the compounds as presently disclosed are compounds of formula (I), or pharmaceutically acceptable salts or adducts thereof, wherein Y is a heterocycloalkyl or heterocycloalkylalkyl. In some still other forms, the compounds as presently disclosed are compounds of formula (I), or pharmaceutically acceptable salts or adducts thereof, wherein the compound of formula (I) has a structure of formula (II):

Formula (II)

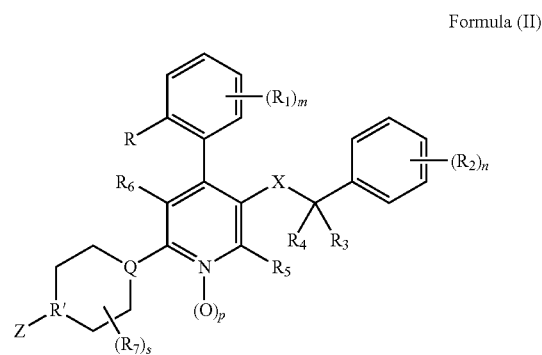

where Q and R' are each independently selected from the group consisting of C, O, S, and N, each optionally independently substituted with one or more independent $R^{103}$ substituents; $R_7$ is selected from the group selected from hydrogen, alkoxy, alkoxyalkyl, —$OR^{101}$, hydroxy, hydroxyalkyl, amino, alkyl, alkenyl, cycloalkyl and halogen, each optionally independently substituted with one or more independent $R^{103}$ substituents; s is from 0 to 4; and all other variables are defined as for formula (I).

In some forms, the compounds as presently disclosed are compounds of formula (I), or pharmaceutically acceptable salts or adducts thereof, wherein the compound of formula (I) has a structure of formula (III):

Formula (III)

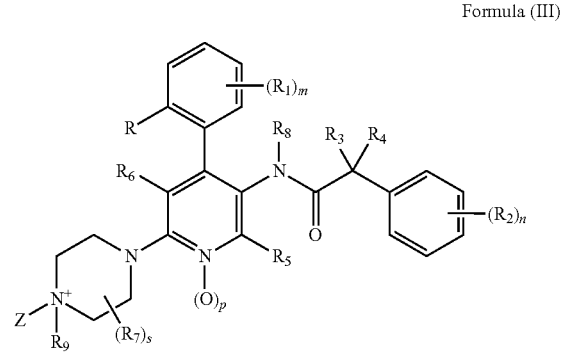

where $R_8$ is selected from the group consisting of hydrogen, alkyl, alkenyl and cycloalkyl, each optionally independently substituted with one or more independent $R^{103}$ substituents; $R_9$ is alkyl or cycloalkyl, each optionally substituted with one or more independent $R^{103}$ substituents; and all other radicals are defined as for formula (I) and formula (II).

In some other forms, the compounds as presently disclosed are compounds of formula (I), or pharmaceutically acceptable salts or adducts thereof, wherein the compound of formula (I) has a structure of formula (IV):

Formula (IV)

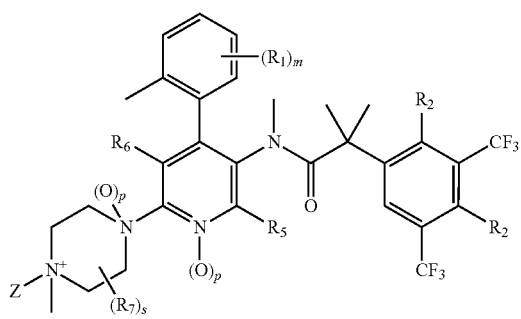

where p is independently 0 or 1; and all other radicals are defined as for formula (I), formula (II) and formula (III).

In some forms, the compounds as presently disclosed are compounds of formula (I), or pharmaceutically acceptable salts or adducts thereof, wherein the compound of formula (I) has a structure of formula (V):

Formula (V)

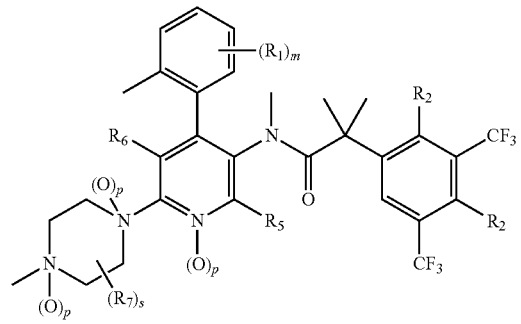

where p is independently 0 or 1; and all other radicals are defined as for formula (I), formula (II), formula (III) and formula (IV).

In some other forms, the compounds as presently disclosed are compounds of formula (I), or pharmaceutically acceptable salts or adducts thereof, wherein the compound of formula (I) has a structure of formula (VI):

Formula (VI)

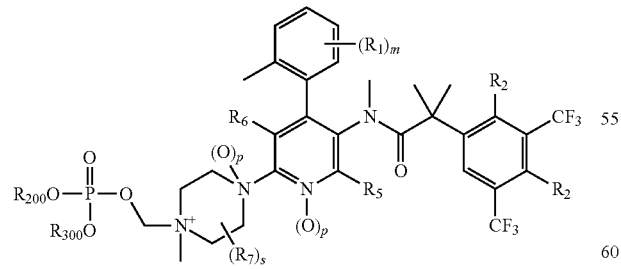

where $R_{200}$ and $R_{300}$ are each independently selected from the group consisting of hydrogen, alkyl and cycloalkyl, each optionally independently substituted with one or more independent $R^{103}$ substituents; or $R_{200}$ and $R_{300}$ are each independently an organic or inorganic cation; p is independently 0 or 1; and all other radicals are defined according to formula (I), formula (II), formula (III), formula (IV) and formula (V).

In some forms, the compounds as presently disclosed are compounds of formula (I), or pharmaceutically acceptable salts or adducts thereof, wherein the compound of formula (I) is a compound selected from the group consisting of:

GA1

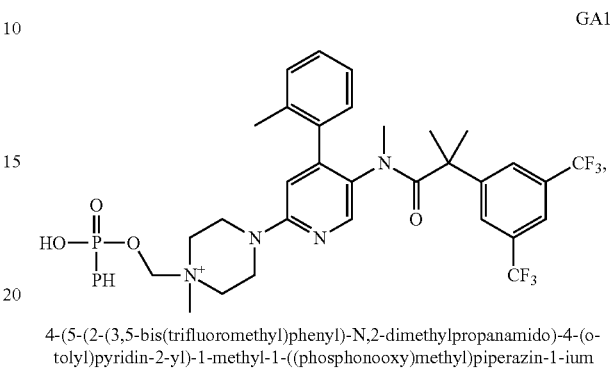

4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium

GA2

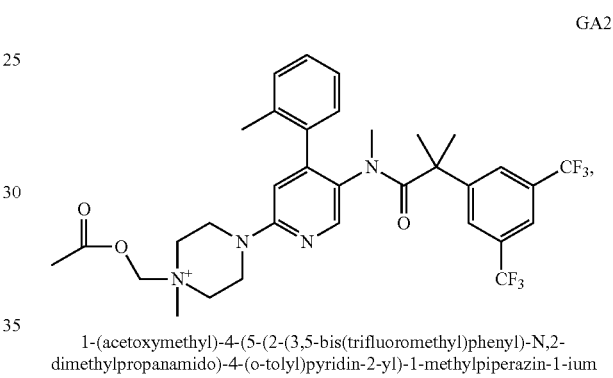

1-(acetoxymethyl)-4-(5-(2-(3,5-bis(trifluoromethyl)phenyl)-N,2-dimethylpropanamido)-4-(o-tolyl)pyridin-2-yl)-1-methylpiperazin-1-ium

GA3

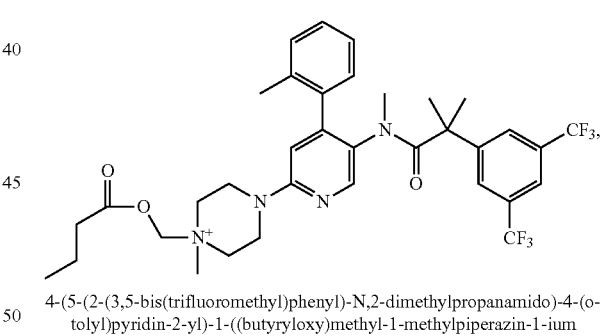

4-(5-(2-(3,5-bis(trifluoromethyl)phenyl)-N,2-dimethylpropanamido)-4-(o-tolyl)pyridin-2-yl)-1-((butyryloxy)methyl-1-methylpiperazin-1-ium

GA4

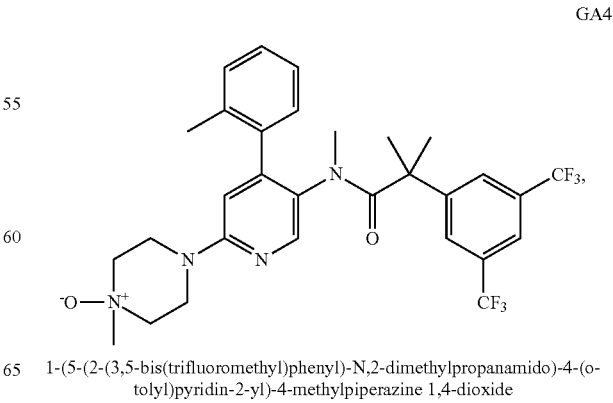

1-(5-(2-(3,5-bis(trifluoromethyl)phenyl)-N,2-dimethylpropanamido)-4-(o-tolyl)pyridin-2-yl)-4-methylpiperazine 1,4-dioxide -continued

GA5

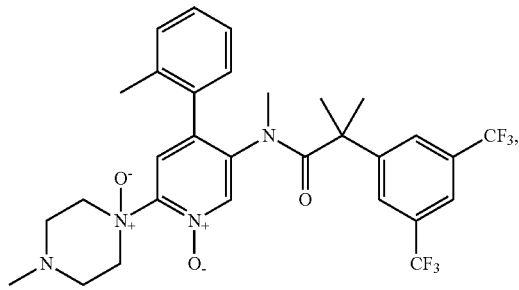

1-(5-(2-(3,5-bis(trifluoromethyl)phenyl)-N,2-dimethylpropanamido)-1-oxido-4-(o-tolyl)pyridin-2-yl)-4-methylpiperazine-1-oxide

GA6

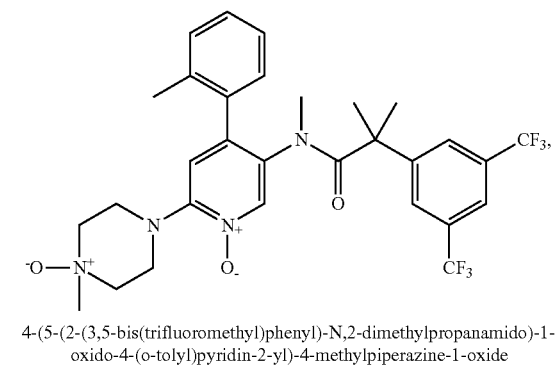

4-(5-(2-(3,5-bis(trifluoromethyl)phenyl)-N,2-dimethylpropanamido)-1-oxido-4-(o-tolyl)pyridin-2-yl)-4-methylpiperazine-1-oxide

GA7

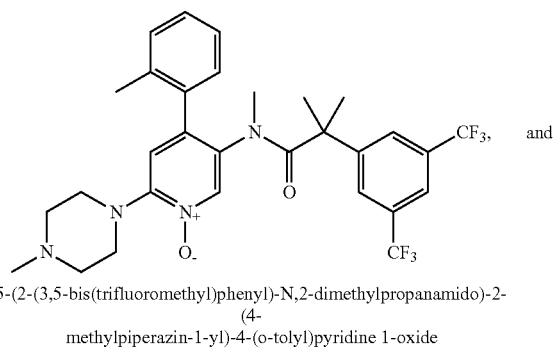

5-(2-(3,5-bis(trifluoromethyl)phenyl)-N,2-dimethylpropanamido)-2-(4-methylpiperazin-1-yl)-4-(o-tolyl)pyridine 1-oxide

GA8

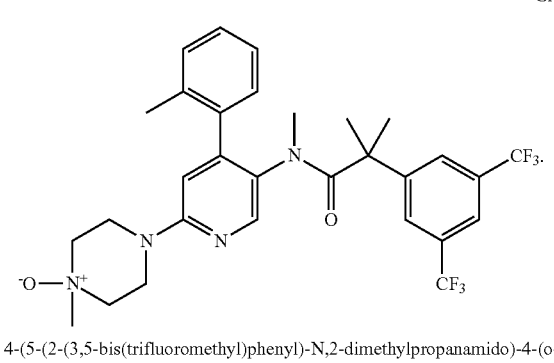

4-(5-(2-(3,5-bis(trifluoromethyl)phenyl)-N,2-dimethylpropanamido)-4-(o-tolyl)pyridin-2-yl)-1-methylpiperazine-1-oxide A particular preferred compound is the chloride hydrochloride HCl salt of GA1 having the following chemical structure which, it has been found, is tremendously resistant to decoupling of the oxo-phosphonomethyl, and reversion of the active moiety to its parent state.

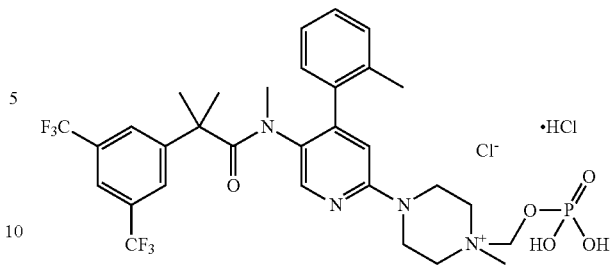

Salts and Adducts

The disclosed compositions and compounds can be used in the form of salts derived from inorganic or organic acids. Depending on the particular compound, a salt of the compound can be advantageous due to one or more of the salt's physical properties, such as enhanced storage stability in differing temperatures and humidities, or a desirable solubility in water or oil. In some instances, a salt of a compound also can be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound, such as the disclosed compounds, with an acid whose anion, or a base whose cation is generally considered suitable for human consumption. Pharmaceutically acceptable salts are particularly useful as products of the disclosed methods because of their greater aqueous solubility relative to the parent compound. For use in medicine, the salts of the disclosed compounds are non-toxic "pharmaceutically acceptable salts." Salts encompassed within the term "pharmaceutically acceptable salts" refer to non-toxic salts of the disclosed compounds which are generally prepared by reacting the free base with a suitable organic or inorganic acid.

Suitable pharmaceutically acceptable acid addition salts of the disclosed compounds, when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclylic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

Furthermore, where the disclosed compounds carry an acidic moiety, suitable pharmaceutically acceptable salts thereof can include alkali metal salts, e.g., sodium or potassium salts; alkaline earth metal salts, e.g., copper, calcium or magnesium salts; and salts formed with suitable organic ligands, e.g., quaternary ammonium salts. In some forms, base salts are formed from bases which form non-toxic salts, including aluminum, arginine, benzathine, choline, diethylamine, diolamine, glycine, lysine, meglumine, olamine, tromethamine and zinc salts.

Organic salts can be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl (C1-C6) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others. In some forms, hemisalts of acids and bases can also be formed, for example, hemisulphate and hemicalcium salts. The disclosed compounds can exist in both unsolvated and solvated forms. A "solvate" as used herein is a nonaqueous solution or dispersion in which there is a noncovalent or easily dispersible combination between solvent and solute, or dispersion means and disperse phase.

The disclosed compositions and compounds can be used in the form of adducts derived by formation of Lewis pairs, covalently linked adducts e.g. between N atoms and carbonyl-containing reactants, hydrates and alcoholates, host-guest adducts containing molecular species not bonded or associated with the medicinal compound, and other clathrates.

Depending on the particular compound, an adduct of the compound can be advantageous due to one or more of the adduct's physical properties, such as enhanced pharmaceutical stability in differing temperatures and humidities, or a desirable solubility in water or oil. In some instances, an adduct of a compound also can be used as an aid in the isolation, purification, and/or resolution of the compound.

Where an adduct is intended to be administered to a patient (as opposed to, for example, being used in an in vitro context), the adduct preferably is pharmaceutically acceptable. The term "pharmaceutically acceptable adduct" refers to an adduct prepared by combining a compound, such as the disclosed compounds, with a gas, water, solvent, Lewis base, carbonyl-containing molecule, or guest molecule that is generally considered suitable for human consumption. Pharmaceutically acceptable addition species are particularly useful as products of the disclosed methods because of their greater aqueous solubility relative to the parent compound. For use in medicine, the adducts of the disclosed compounds are non-toxic "pharmaceutically acceptable adducts." Adducts encompassed within the term "pharmaceutically acceptable salts" refer to non-toxic adducts of the disclosed compounds which are generally prepared by reacting a compound of the invention with a suitable organic or inorganic addition species.

Suitable pharmaceutically acceptable adducts of the disclosed compounds, when possible, include those derived from Lewis bases such as boric acid, aluminum hydroxide, organic sulfoxides, organic sulfones, organic sulfonium salts, $H_3PO_3$, siloxanes, and other Lewis bases.

Suitable pharmaceutically acceptable adducts of the disclosed compounds, when possible, also include those derived from covalent bonding between an oxygen, nitrogen or sulfur atom of the compound and carbon dioxide, low alkyl aldehyde or ketone, vanillin, amino acid, or a nucleic acid.

Suitable pharmaceutically acceptable adducts of the disclosed compounds, when possible, also include those derived from inclusion of an unbonded gas such as dioxygen, dinitrogen, carbon dioxide, nitrous oxide, ethyl ether, or other gas, contained within but not bonded to a crystalline or amorphous phase of the compound.

Suitable pharmaceutically acceptable adducts of the disclosed compounds, when possible, also include those derived from association of a molecule of the compound with water, a pharmaceutically acceptable lower alkyl alcohol, or another pharmaceutically acceptable solvent that is associated in a molecular ratio with the compound.

In one embodiment the adduct is optionally a clathrate.

General Synthetic Schemes

The compounds of the formula (I) (and other disclosed compounds), or their pharmaceutically acceptable salts or adducts, can be prepared by the methods as illustrated by examples described in the "Examples" section, together with synthetic methods known in the art of organic chemistry, or modifications and derivatisations that are familiar to those of ordinary skill in the art. The starting materials used herein are commercially available or can be prepared by routine methods known in the art (such as those methods disclosed in standard reference books such as the Compendium of Organic Synthesis Methods, Vol. I-VI (published by Wiley-Interscience)). Preferred methods include, but are not limited to, those described below. During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, T. W.

Greene and P. G. M. Wuts, Protective Groups in Organic Chemistry, John Wiley & Sons, 1999, and P. G. M. Wuts and T. W. Greene, Protective Groups in Organic Chemistry, John Wiley & Sons, 2006. Isolation and purification of the products is accomplished by standard procedures, which are known to a chemist of ordinary skill.

The invention further provides methods for making suitable prodrugs of the 4-phenyl-pyridine derivatives. In one embodiment the invention provides a one-step, acid-free synthesis for functionalizing tertiary amines by reaction with chloromethyl dialkyl phosphate esters to create (phosphooxy)methyl prodrugs that are substrates for phosphatase enzymes. By contrast the prior art had required multiple synthetic steps for comparable reactions, including requiring the use of proton scavengers during initial reaction and requiring strong acid to deprotect the phosphate group in another step. In another embodiment the invention provides methods for making chloromethyl dialkyl phosphate esters having suitable purity and economy, because the quality of phosphate ester compositions from commercial sources is too low to provide acceptable yields for reactions according to the invention. In an additional embodiment the invention provides a method to stabilize the (phosphooxy)methyl prodrugs according to the invention by combination with two equivalents of hydrochloric acid, because whereas the prior art preferred the use of dibasic salts of (phosphooxy)methyl substituents for quaternary ammonium salts in prodrugs, the present invention had found that such salts are unstable and reform the underlying drug during storage.

DEFINITION OF TERMS

The term "alkyl" refers to a linear or branched-chain saturated hydrocarbyl substituent (i.e., a substituent obtained from a hydrocarbon by removal of a hydrogen) containing from one to twenty carbon atoms; in one embodiment from one to twelve carbon atoms; in another embodiment, from one to ten carbon atoms; in another embodiment, from one to six carbon atoms; and in another embodiment, from one to four carbon atoms. Examples of such substituents include methyl, ethyl, propyl (including n-propyl and isopropyl), butyl (including n-butyl, isobutyl, sec-butyl and tert-butyl), pentyl, iso-amyl, hexyl and the like.

The term "alkenyl" refers to a linear or branched-chain hydrocarbyl substituent containing one or more double bonds and from two to twenty carbon atoms; in another embodiment, from two to twelve carbon atoms; in another embodiment, from two to six carbon atoms; and in another embodiment, from two to four carbon atoms. Examples of alkenyl include ethenyl (also known as vinyl), allyl, propenyl (including 1-propenyl and 2-propenyl) and butenyl (including 1-butenyl, 2-butenyl and 3-butenyl). The term "alkenyl" embraces substituents having "cis" and "trans" orientations, or alternatively, "E" and "Z" orientations.

The term "benzyl" refers to methyl radical substituted with phenyl.

The term "carbocyclic ring" refers to a saturated cyclic, partially saturated cyclic, or aromatic ring containing from 3 to 14 carbon ring atoms ("ring atoms" are the atoms bound together to form the ring). A carbocyclic ring typically contains from 3 to 10 carbon ring atoms. Examples include cyclopropyl, cyclobutyl, cyclopentyl, cyclopentenyl, cyclopentadienyl, cyclohexyl, cyclohexenyl, cyclohexadienyl, and phenyl. A "carbocyclic ring system" alternatively may be 2 or 3 rings fused together, such as naphthalenyl, tetrahydronaphthalenyl (also known as "tetralinyl"), indenyl, isoindenyl, indanyl, bicyclodecanyl, anthracenyl, phenanthrene, benzonaphthenyl (also known as "phenalenyl"), fluorenyl, and decalinyl.

The term "heterocyclic ring" refers to a saturated cyclic, partially saturated cyclic, or aromatic ring containing from 3 to 14 ring atoms ("ring atoms" are the atoms bound together to form the ring), in which at least one of the ring atoms is a heteroatom that is oxygen, nitrogen, or sulfur, with the remaining ring atoms being independently selected from the group consisting of carbon, oxygen, nitrogen, and sulfur.

The term "cycloalkyl" refers to a saturated carbocyclic substituent having three to fourteen carbon atoms. In one embodiment, a cycloalkyl substituent has three to ten carbon atoms. Examples of cycloalkyl include cyclopropyl, cyclobutyl, cyclopentyl and cyclohexyl.

The term "cycloalkyl" also includes substituents that are fused to a $C_6$-$C_{10}$ aromatic ring or to a 5-10-membered heteroaromatic ring, wherein a group having such a fused cycloalkyl group as a substituent is bound to a carbon atom of the cycloalkyl group. When such a fused cycloalkyl group is substituted with one or more substituents, the one or more substituents, unless otherwise specified, are each bound to a carbon atom of the cycloalkyl group. The fused $C_6$-$C_{10}$ aromatic ring or to a 5-10-membered heteroaromatic ring may be optionally substituted with halogen, $C_1$-$C_6$ alkyl, $C_3$-$C_{10}$ cycloalkyl, or =O.

The term "cycloalkenyl" refers to a partially unsaturated carbocyclic substituent having three to fourteen carbon atoms, typically three to ten carbon atoms. Examples of cycloalkenyl include cyclobutenyl, cyclopentenyl, and cyclohexenyl.

A cycloalkyl or cycloalkenyl may be a single ring, which typically contains from 3 to 6 ring atoms. Examples include cyclopropyl, cyclobutyl, cyclopentyl, cyclopentenyl, cyclopentadienyl, cyclohexyl, cyclohexenyl, cyclohexadienyl, and phenyl. Alternatively, 2 or 3 rings may be fused together, such as bicyclodecanyl and decalinyl.

The term "aryl" refers to an aromatic substituent containing one ring or two or three fused rings. The aryl substituent may have six to eighteen carbon atoms. As an example, the aryl substituent may have six to fourteen carbon atoms. The term "aryl" may refer to substituents such as phenyl, naphthyl and anthracenyl. The term "aryl" also includes substituents such as phenyl, naphthyl and anthracenyl that are fused to a $C_4$-$C_{10}$ carbocyclic ring, such as a $C_5$ or a $C_6$ carbocyclic ring, or to a 4-10-membered heterocyclic ring, wherein a group having such a fused aryl group as a substituent is bound to an aromatic carbon of the aryl group. When such a fused aryl group is substituted with one more substituents, the one or more substituents, unless otherwise specified, are each bound to an aromatic carbon of the fused aryl group. The fused $C_4$-$C_{10}$ carbocyclic or 4-10-membered heterocyclic ring may be optionally substituted with halogen, $C_1$-$C_6$ alkyl, $C_3$-$C_{10}$ cycloalkyl, or =O. Examples of aryl groups include accordingly phenyl, naphthalenyl, tetrahydronaphthalenyl (also known as "tetralinyl"), indenyl, isoindenyl, indanyl, anthracenyl, phenanthrenyl, benzonaphthenyl (also known as "phenalenyl"), and fluorenyl.

In some instances, the number of carbon atoms in a hydrocarbyl substituent (e.g., alkyl, alkenyl, cycloalkyl, cycloalkenyl, aryl, etc.) is indicated by the prefix "$C_x$-$C_y$—," wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl refers to saturated cycloalkyl containing from 3 to 6 carbon ring atoms.

In some instances, the number of atoms in a cyclic substituent containing one or more heteroatoms (e.g., heteroaryl or heterocycloalkyl) is indicated by the prefix "X-Y-membered", wherein x is the minimum and y is the maximum number of atoms forming the cyclic moiety of the substituent. Thus, for example, 5-8-membered heterocycloalkyl refers to a heterocycloalkyl containing from 5 to 8 atoms, including one or more heteroatoms, in the cyclic moiety of the heterocycloalkyl.

The term "hydrogen" refers to hydrogen substituent, and may be depicted as —H.

The term "hydroxy" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "hydroxyalkyl" refers to an alkyl that is substituted with at least one hydroxy substituent. Examples of hydroxyalkyl include hydroxymethyl, hydroxyethyl, hydroxypropyl and hydroxybutyl.

The term "nitro" means —$NO_2$.
The term "cyano" (also referred to as "nitrile") —CN.
The term "carbonyl" means —C(O)—.
The term "amino" refers to —$NH_2$.
The term "alkylamino" refers to an amino group, wherein at least one alkyl chain is bonded to the amino nitrogen in place of a hydrogen atom. Examples of alkylamino substituents include monoalkylamino such as methylamino (exemplified by the formula —NH(CH$_3$)), and dialkylamino such as dimethylamino.

The term "aminocarbonyl" means —C(O)—NH$_2$.

The term "halogen" refers to fluorine (which may be depicted as —F), chlorine (which may be depicted as —Cl), bromine (which may be depicted as —Br), or iodine (which may be depicted as —I). In one embodiment, the halogen is chlorine. In another embodiment, the halogen is a fluorine.

The prefix "halo" indicates that the substituent to which the prefix is attached is substituted with one or more independently selected halogen substituents. For example, haloalkyl refers to an alkyl that is substituted with at least one halogen substituent. The term "oxo" refers to =O.

The term "oxy" refers to an ether substituent, and may be depicted as —O—.

The term "alkoxy" refers to an alkyl linked to an oxygen, which may also be represented as —O—R, wherein the R represents the alkyl group. Examples of alkoxy include methoxy, ethoxy, propoxy and butoxy.

The term "alkylthio" means —S-alkyl. For example, "methylthio" is —S—CH$_3$. Other examples of alkylthio include ethylthio, propylthio, butylthio, and hexylthio.

The term "alkylcarbonyl" means —C(O)-alkyl. Examples of alkylcarbonyl include methylcarbonyl, propylcarbonyl, butylcarbonyl, pentylcabonyl, and hexylcarbonyl.

The term "aminoalkcylcarbonyl" means —C(O)-alkyl-NH$_2$.

The term "alkoxycarbonyl" means —C(O)—O-alkyl. Examples of alkoxycarbonyl include methoxycarbonyl, ethoxycarbonyl, propoxycarbonyl, butoxycarbonyl, pentoxycarbonyl, and hexyloxycarbonyl. In another embodiment, where the carbon atom of the carbonyl is attached to a carbon atom of a second alkyl, the resulting functional group is an ester.

The terms "thio" and "thia" mean a divalent sulfur atom and such a substituent may be depicted as —S—. For example, a thioether is represented as "alkyl-thio-alkyl" or, alternatively, alkyl-S-alkyl.

The term "thiol" refers to a sulfhydryl substituent, and may be depicted as —SH.

The term "thione" refers to =S.

The term "sulfonyl" refers to —S(O)$_2$—. Thus, for example, "alkyl-sulfonyl-alkyl" refers to alkyl-S(O)$_2$-alkyl. Examples of alkylsulfonyl include methylsulfonyl, ethylsulfonyl, and propylsulfonyl.

The term "aminosulfonyl" means —S(O)$_2$—NH$_2$.

The term "sulfinyl" or "sulfoxido" means —S(O)—. Thus, for example, "alkylsulfinylalkyl" or "alkylsulfoxidoalkyl" refers to alkyl-S(O)-alkyl. Exemplary alkylsulfinyl groups include methylsulfinyl, ethylsulfinyl, butylsulfinyl, and hexylsulfinyl.

The term "heterocycloalkyl" refers to a saturated or partially saturated ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocycloalkyl alternatively may comprise 2 or 3 rings fused together, wherein at least one such ring contains a heteroatom as a ring atom (e.g., nitrogen, oxygen, or sulfur). In a group that has a heterocycloalkyl substituent, the ring atom of the heterocycloalkyl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom.

Examples of heterocycloalkyl include, but not limited to, azacyclobutane, 1,3-diazatidine, pyrrolidine, 2-pyrroline, 3-pyrroline, 2-imidazoline, imidazolidine, 2-pyrazoline, pyrazolidine, piperidine, 1,2-diazacyclohexane, 1,3-diazacyclohexane, 1,4-diazacyclohexane, octahydroazocine, oxacyclobutane, tetrahydrofuran, tetrahydropyran, 1,2-dioxacyclohexane, 1,3-dioxacyclohexane, 1,4-dioxacyclohexane, 1,3-dioxolane, thiacyclobutane, thiocyclopentane, 1,3-dithiolane, thiacyclohexane, 1,4-dithiane, 1,3-oxathialane, morpholine, 1,4-thiaxane, 1,3,5-trithiane and thiomorpholine.

The term "heterocycloalkyl" also includes substituents that are fused to a $C_6$-$C_{10}$ aromatic ring or to a 5-10-membered heteroaromatic ring, wherein a group having such a fused heterocycloalkyl group as a substituent is bound to a heteroatom of the heterocyclocalkyl group or to a carbon atom of the heterocycloalkyl group. When such a fused heterocycloalkyl group is substituted with one more substituents, the one or more substituents, unless otherwise specified, are each bound to a heteroatom of the heterocyclocalkyl group or to a carbon atom of the heterocycloalkyl group. The fused $C_6$-$C_{10}$ aromatic ring or to a 5-10-membered heteroaromatic ring may be optionally substituted with halogen, $C_1$-$C_6$ alkyl, $C_3$-$C_{10}$ cycloalkyl, or =O.

The term "heteroaryl" refers to an aromatic ring structure containing from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings. Examples of heteroaryl substituents include 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as quinolinyl, isoquinolinyl, cinnolinyl, quinazolinyl, and 1,4-benzoxazinyl. The term "heteroaryl" also includes pyridyl N-oxides and groups containing a pyridine N-oxide ring.

Examples of single-ring heteroaryls include furanyl, dihydrofuranyl, tetradydrofuranyl, thiophenyl (also known as "thiofuranyl"), dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaediazolyl, oxathiazolyl, oxadiazolyl (including oxadiazolyl, 1,2,4-oxadiazolyl (also known as "azoximyl"), 1,2,5-oxadiazolyl (also known as "furazanyl"), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl (including 1,2-pyranyl or 1,4-pyranyl), dihydropyranyl, pyridinyl (also known as "azinyl"), piperidinyl, diazinyl (including pyridazinyl (also known as "1,2-diazinyl"), pyrimidinyl (also known as "1,3-diazinyl" or "pyrimidyl"), or pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl")), oxazinyl (including 1,2,3-oxazinyl, 1,3,2-oxazinyl, 1,3,6-oxazinyl (also known as "pentoxazolyl"), 1,2,6-oxazinyl, or 1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl or 1,3,5,2-oxadiazinyl), morpholinyl, azepinyl, oxepinyl, thiepinyl, and diazepinyl.

Examples of 2-fused-ring heteroaryls include, indolizinyl, pyrindinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl.

Examples of 3-fused-ring heteroaryls or heterocycloalkyls include 5,6-dihydro-4H-imidazo[4,5,1-ij]quinoline, 4,5-dihydroimidazo[4,5,1-hi]indole, 4,5,6,7-tetrahydroimidazo[4,5,1-jk][1]benzazepine, and dibenzofuranyl.

The term "heteroaryl" also includes substituents such as pyridyl and quinolinyl that are fused to a $C_4$-$C_{10}$ carbocyclic ring, such as a $C_5$ or a $C_6$ carbocyclic ring, or to a 4-10-membered heterocyclic ring, wherein a group having such a fused aryl group as a substituent is bound to an aromatic carbon of the heteroaryl group or to a heteroatom of the heteroaryl group. When such a fused heteroaryl group is substituted with one more substituents, the one or more substituents, unless otherwise specified, are each bound to an aromatic carbon of the heteroaryl group or to a heteroatom of the heteroaryl group. The fused $C_4$-$C_{10}$ carbocyclic or 4-10-membered heterocyclic ring may be optionally substituted with halogen, $C_1$-$C_6$ alkyl, $C_3$-$C_{10}$ cycloalkyl, or =O.

The term "ethylene" refers to the group —$CH_2$—$CH_2$—. The term "ethynelene" refers to the group —CH=CH—. The term "propylene" refers to the group —$CH_2$—$CH_2$—$CH_2$—. The term "butylene" refers to the group —$CH_2$—$CH_2$—$CH_2$—$CH_2$—. The term "methylenoxy" refers to the group —$CH_2$—O—. The term "methylenethioxy" refers to the group —$CH_2$—S—. The term "methylenamino" refers to the group —$CH_2$—N(H)—. The term "ethylenoxy" refers to the group —$CH_2$—$CH_2$—O—. The term "ethylenethioxy" refers to the group —$CH_2$—$CH_2$—S—. The term "ethylenamino" refers to the group —$CH_2$—$CH_2$—N(H)—.

A substituent is "substitutable" if it comprises at least one carbon, sulfur, oxygen or nitrogen atom that is bonded to one or more hydrogen atoms. Thus, for example, hydrogen, halogen, and cyano do not fall within this definition. If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent.

If a substituent is described as being "optionally substituted," the substituent may be either (1) not substituted, or (2) substituted. When a substituent is comprised of multiple moieties, unless otherwise indicated, it is the intention for the final moiety to serve as the point of attachment to the remainder of the molecule. For example, in a substituent A-B-C, moiety C is attached to the remainder of the molecule. If substituents are described as being "independently selected" from a group, each substituent is selected independent of the other. Each substituent therefore may be identical to or different from the other substituent(s).

Pharmaceutical Compositions

Pharmaceutical compositions for preventing and/or treating a subject are further provided comprising a therapeutically effective amount of a compound of formula (I), or a pharmaceutically acceptable salt or adduct thereof, and one or more pharmaceutically acceptable excipients.

A "pharmaceutically acceptable" excipient is one that is not biologically or otherwise undesirable, i.e., the material can be administered to a subject without causing any undesirable biological effects or interacting in a deleterious manner with any of the other components of the pharmaceutical composition in which it is contained. The carrier can be selected to minimize any degradation of the active ingredient and to minimize any adverse side effects in the subject, as would be well known to one of skill in the art. The carrier can be a solid, a liquid, or both.

The disclosed compounds can be administered by any suitable route, preferably in the form of a pharmaceutical composition adapted to such a route, and in a dose effective for the treatment or prevention intended. The active compounds and compositions, for example, can be administered orally, rectally, parenterally, ocularly, inhalationaly, or topically. In particular, administration can be epicutaneous, inhalational, enema, conjunctival, eye drops, ear drops, alveolar, nasal, intranasal, vaginal, intravaginal, transvaginal, ocular, intraocular, transocular, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc.

Suitable carriers and their formulations are described in *Remington: The Science and Practice of Pharmacy* (19th ed.) ed. A. R. Gennaro, Mack Publishing Company, Easton, Pa., 1995. Oral administration of a solid dose form can be, for example, presented in discrete units, such as hard or soft capsules, pills, cachets, lozenges, or tablets, each containing a predetermined amount of at least one of the disclosed compound or compositions. In some forms, the oral administration can be in a powder or granule form. In some forms, the oral dose form is sub-lingual, such as, for example, a lozenge. In such solid dosage forms, the compounds of formula I are ordinarily combined with one or more adjuvants. Such capsules or tablets can contain a controlled-release formulation. In the case of capsules, tablets, and pills, the dosage forms also can comprise buffering agents or can be prepared with enteric coatings.

In some forms, oral administration can be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also can comprise adjuvants, such as wetting, emulsifying, suspending, flavoring (e.g., sweetening), and/or perfuming agents.

In some forms, the disclosed compositions can comprise a parenteral dose form. "Parenteral administration" includes, for example, subcutaneous injections, intravenous injections, intraperitoneally, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Typically, an appropriate amount of a pharmaceutically acceptable carrier is used in the formulation to render the formulation isotonic. Examples of the pharmaceutically acceptable carrier include, but are not limited to, saline, Ringer's solution and dextrose solution. Other acceptable excipients include, but are not limited to, thickeners, diluents, buffers, preservatives, surface active agents and the like.

Other carrier materials and modes of administration known in the pharmaceutical art can also be used. The disclosed pharmaceutical compositions can be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

The disclosed compounds can be used, alone or in combination with other therapeutic agents, in the treatment or prevention of various conditions or disease states. The administration of two or more compounds "in combination" means that the two compounds are administered closely enough in time that the presence of one alters the biological effects of the other. The two or more compounds can be administered simultaneously, concurrently or sequentially.

Disclosed are pharmaceutical compositions comprising an effective amount of a compound of the invention or a pharmaceutically accepted salt, solvate, clathrate, or prodrug thereof; and a pharmaceutically acceptable carrier or vehicle. These compositions may further comprise additional agents. These compositions are useful for modulating the activity of the neurokinin ($NK_1$) receptor, thus to improve the prevention and treatment of $NK_1$ receptor associated diseases such as nausea and vomiting, bladder dysfunction, depression or anxiety.

In some forms, disclosed are pharmaceutical compositions for preventing and/or treating a subject comprising a therapeutically effective amount of a compound according to formula (I), and one or more pharmaceutically acceptable excipients. In some other forms, disclosed are pharmaceutical compositions, further comprising one or more therapeutic agents or a pharmaceutically acceptable salt thereof. In some forms, said therapeutic agent is a $5-HT_3$ antagonist, a $NK_1$ antagonist or dexamethasone. In some other forms, said $5-HT_3$ antagonist is ondansetron, palonosetron, granisetron or tropisetron, or a pharmaceutically acceptable salt thereof.

Methods

All of the methods of the invention may be practiced with a compound of the invention alone, or in combination with other agents.

Treating

The above-described compounds and compositions are useful for the inhibition, reduction, prevention, and/or treatment of diseases which are pathophysiologically modulated by the neurokinin ($NK_1$) receptor. Accordingly, in some forms, disclosed are methods of preventing and/or treating diseases which are pathophysiologically modulated by the $NK_1$ receptor, comprising administering to a subject a therapeutically effective amount of a compound of formula (I) as disclosed above, or a pharmaceutically acceptable salt or adduct thereof.

Suitable subjects can include mammalian subjects. Mammals include, but are not limited to, canine, feline, bovine, caprine, equine, ovine, porcine, rodents, lagomorphs, primates, and the like, and encompass mammals in utero. In some forms, humans are the subjects. Human subjects can be of either gender and at any stage of development.

In some other forms, disclosed are methods of preventing and/or treating diseases which are pathophysiologically modulated by the $NK_1$ receptor, wherein said disease is nausea and vomiting, bladder dysfunction, depression or anxiety.

In some other forms, disclosed are methods of preventing and/or treating diseases which are pathophysiologically modulated by the $NK_1$ receptor, wherein said nausea and vomiting is chemotherapy induced nausea and vomiting (CINV), radiation therapy induced nausea and vomiting (RINV), or post-operative nausea and vomiting (PONV).

In some other forms, disclosed are methods of preventing and/or treating diseases which are pathophysiologically modulated by the $NK_1$ receptor, wherein said nausea and vomiting is induced by moderately or highly emetogenic chemotherapy. In some other forms, disclosed are methods of preventing and/or treating diseases which are pathophysiologically modulated by the $NK_1$ receptor, wherein said nausea and vomiting is an acute and/or delayed phases of CINV.

Acute emesis refers to the first twenty-four hour period following an emesis-inducing event. Delayed emesis refers to the second, third, fourth and fifth twenty-four hour periods following an emesis-inducing event. When a treatment is said to be effective during the delayed phase, it will be understood to mean that the effectiveness of the treatment is statistically significant during the entire delayed phase, regardless of whether the treatment is effective during any particular twenty-four hour period of the delayed phase. It will also be understood that the method can be defined based upon its effectiveness during any one of the twenty-four hour periods of the delayed phase. Thus, unless otherwise specified, any of the methods of treating nausea and/or vomiting during the delayed phases, as described herein, could also be practiced to treat nausea and/or vomiting during the second, third, fourth or fifth twenty-four hour periods following an emesis inducing event, or an combination thereof.

In some other forms, disclosed are methods of preventing and/or treating diseases which are pathophysiologically modulated by the $NK_1$ receptor, wherein said acute and/or delayed phases of CINV is induced by moderately or highly emetogenic chemotherapy. "Highly emetogenic chemotherapy" refers to chemotherapy having a high degree of emetogenic potential, and includes chemotherapy based on carmustine, cisplatin, cyclophosphamide≥1500 mg/m$^2$, dacarbazine, dactinomycin, mechlorethamine, and streptozotocin. "Moderately emetogenic chemotherapy" refers to chemotherapy having a moderate degree of emetogenic potential, and includes chemotherapy based on carboplatin, cyclophosphamide<1500 mg/m$^2$, cytarabine>1 mg/m$^2$, daunorubicin, doxorubicin, epirubicin, idarubicin, ifosfamide, irinotecan, and oxaliplatin.

In a preferred embodiment, the methods of the present invention are effective to treat acute and delayed emesis resulting from moderately and highly emetogenic chemotherapy, from a single dose of the netupitant derivative administered prior to chemotherapy, optionally in combination with other active ingredients.

A particularly preferred regimen for treating emesis, especially emesis induced by chemotherapy, involves a netupitant derivative of the present invention, a 5-HT3 antagonist such as palonosetron or a pharmaceutically acceptable salt thereof, and a corticosteroid such as dexamethasone. A suitable fixed regimen for treating acute and delayed CINV includes a single administration of the netupitant derivative on day one (preferably before chemotherapy), a single administration of the 5-HT3 antagonist on day 1 (preferably before chemotherapy). A corticosteroid is optionally added to the combination on day one and, when highly emetogenic chemotherapy is administered, on days 2, 3 and 4 as well. A preferred intravenous dose of palonosetron HCl is 0.25 mg based on the weight of the free base. Preferred dexamethasone doses are 12 mg. orally on day 1, followed by 8 mg. orally on days 2, 3 and 4 for highly emetogenic chemotherapy.

In some other forms, disclosed are methods of preventing and/or treating diseases which are pathophysiologically modulated by the $NK_1$ receptor, wherein said bladder dysfunction is selected from urgency, frequency, pollakiuria, nocturia, low deferment time, suboptimal volume threshold, and neurogenic bladder, or a combination thereof.

In some other forms, disclosed are methods of preventing and/or treating diseases which are pathophysiologically modulated by the $NK_1$ receptor, wherein said compound or a pharmaceutically acceptable salt or adduct thereof, is administered by one or more routes selected from the group consisting of rectal, buccal, sublingual, intravenous, subcutaneous, intradermal, transdermal, intraperitoneal, oral, eye drops, parenteral and topical administration.

In some other forms, disclosed are methods of preventing and/or treating diseases which are pathophysiologically modulated by the $NK_1$ receptor, wherein said administration is accomplished by intravenously administering a liquid form of said compound or a pharmaceutically acceptable salt or adduct thereof.

In some other forms, disclosed are methods of preventing and/or treating diseases which are pathophysiologically modulated by the $NK_1$ receptor, particularly by derivatives of netupitant, wherein said administration is accomplished by orally administering said compound or a pharmaceutically acceptable salt or adduct thereof. In some other forms, disclosed are methods of preventing and/or treating diseases which are pathophysiologically modulated by the $NK_1$ receptor, wherein said netupitant derivative is orally administered at a dosage of from about 50 mg to about 500 mg, from about 100 mg to about 400 mg, from about 150 mg to about 350 mg, or about 300 mg, based on the weight of the netupitant component of the molecule.

In some other forms, disclosed are methods of preventing and/or treating diseases which are pathophysiologically modulated by the $NK_1$ receptor, particularly by derivatives of netupitant, wherein said compound or a pharmaceutically acceptable salt or adduct thereof is intravenously administered at a dosage of from about 10 mg to about 200 mg, from about 50 mg to about 150 mg, from about 75 mg to about 125 mg, or about 100 mg, based on the weight of the netupitant component of the molecule.

In some other forms, disclosed are methods of preventing and/or treating diseases which are pathophysiologically modulated by the $NK_1$ receptor, particularly by derivatives of netupitant, wherein said compound or a pharmaceutically acceptable salt or adduct thereof, is formulated to have a concentration of from about 1 to about 20 mg/ml, from about 5 to about 15 mg/ml, from about 7 to about 2 mg/ml, or about 10 mg/ml, based on the weight of the netupitant component of the molecule.

In some other forms, disclosed are methods of preventing and/or treating diseases which are pathophysiologically modulated by the $NK_1$ receptor, wherein said compound or a pharmaceutically acceptable salt or adduct thereof, is administered in a single dosage per day, a single dosage during a multi-day course of therapy (e.g., a five-day therapeutic regimen for delayed emesis), or in multiple dosages per day. In some other forms, disclosed are methods of preventing and/or treating diseases which are pathophysiologically modulated by the $NK_1$ receptor, wherein said multiple dosages are from 2 to 4 dosages per day.

In some other forms, disclosed are methods of preventing and/or treating diseases which are pathophysiologically modulated by the $NK_1$ receptor, further comprising administering one or more therapeutic agents or a pharmaceutically acceptable salt thereof. In some other forms, said therapeutic agent is a $5-HT_3$ antagonist, a $NK_1$ antagonist or dexamethasone. In some other forms, said $5-HT_3$ antagonist is ondansetron, palonosetron, granisetron or tropisetron, or a pharmaceutically acceptable salt thereof. In some still other forms, said $5-HT_3$ antagonist is palonosetron or a pharmaceutically acceptable salt thereof. In some other forms, the oral dosage of palonosetron or a pharmaceutically acceptable salt thereof is from about 0.1 mg to about 2.0 mg, from about 0.25 mg to about 1.0 mg, from about 0.5 mg to about 0.75 mg, or about 0.5 mg. In some other forms, the intravenous dosage of palonosetron or a pharmaceutically acceptable salt thereof is from about 0.05 mg to about 2.0 mg, from about 0.075 mg to about 1.5 mg, from about 0.1 mg to about 1.0 mg, from about 0.25 mg to about 0.75 mg, or about 0.25 mg. In some other forms, said palonosetron or a pharmaceutically acceptable salt thereof is formulated to have a concentration of about 0.25 mg/5 mL.

In some other forms, disclosed are methods of preventing and/or treating diseases which are pathophysiologically modulated by the $NK_1$ receptor, further comprising administering one or more therapeutic agents or a pharmaceutically acceptable salt thereof, wherein said therapeutic agent is a $NK_1$ antagonist which is 2-(3,5-bis(trifluoromethyl)phenyl)-N,2-dimethyl-N-(6-(4-methylpiperazin-1-yl)-4-(o-tolyl)pyridin-3-yl)propanamide (netupitant). In one embodiment, the netupitant is administered in combination with GA8, and the ratio of GA8 to netupitant is greater than 1:200 or 1:100.

In some other forms, disclosed are methods of preventing and/or treating diseases which are pathophysiologically modulated by the $NK_1$ receptor, wherein the subject is a human. In some other forms, disclosed are methods of preventing and/or treating diseases which are pathophysiologically modulated by the $NK_1$ receptor, wherein the subject has been identified as needing treatment for the disease or the administration.

One of ordinary skill in the art of treating such diseases will be able, without undue experimentation and in reliance upon personal knowledge and the disclosure of this application, to ascertain a therapeutically effective amount of a compound of Formula I for a given disease. In some other forms, disclosed are methods of preventing and/or treating a subject, further comprising one or more therapeutic agents.

More Definitions of Terms

1. A, an, the

As used in the specification and the appended claims, the singular forms "a," "an" and "the" include plural referents unless the context clearly dictates otherwise. Thus, for example, reference to "a pharmaceutical carrier" includes not only single carriers but also mixtures of two or more such carriers, and the like.

2. Abbreviations

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, "M" for molar, and like abbreviations).

3. About

The term "about," when used to modify the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. Whether modified by the term "about" the claims appended hereto include equivalents to these quantities.

4. Comprise

Throughout the description and claims of this specification, the word "comprise" and variations of the word, such as "comprising" and "comprises," means "including but not limited to," and is not intended to exclude, for example, other additives, components, integers or steps.

5. Publications

Throughout this application, various publications are referenced. In order to more fully document the state of the art to which this invention pertains, the disclosures of these publications are to be considered as being referenced individually, specifically and in their entireties for the material contained in them that is discussed in the sentence in which the reference is relied upon.

6. Subject

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Preparation of Compounds of Formula (I)

The following are examples of preparation of compounds of formula (I). This example is intended to be purely exemplary and is not intended to limit the disclosure.

General Scheme of Preparing Compounds of Formula (I)

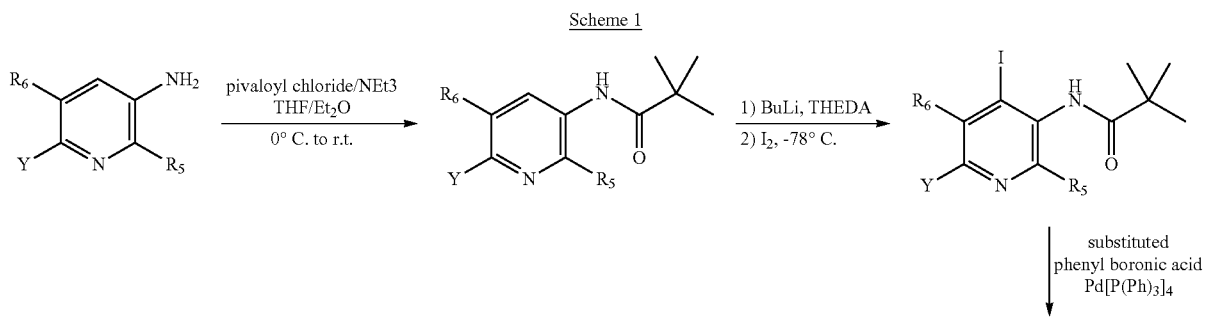

Scheme 1

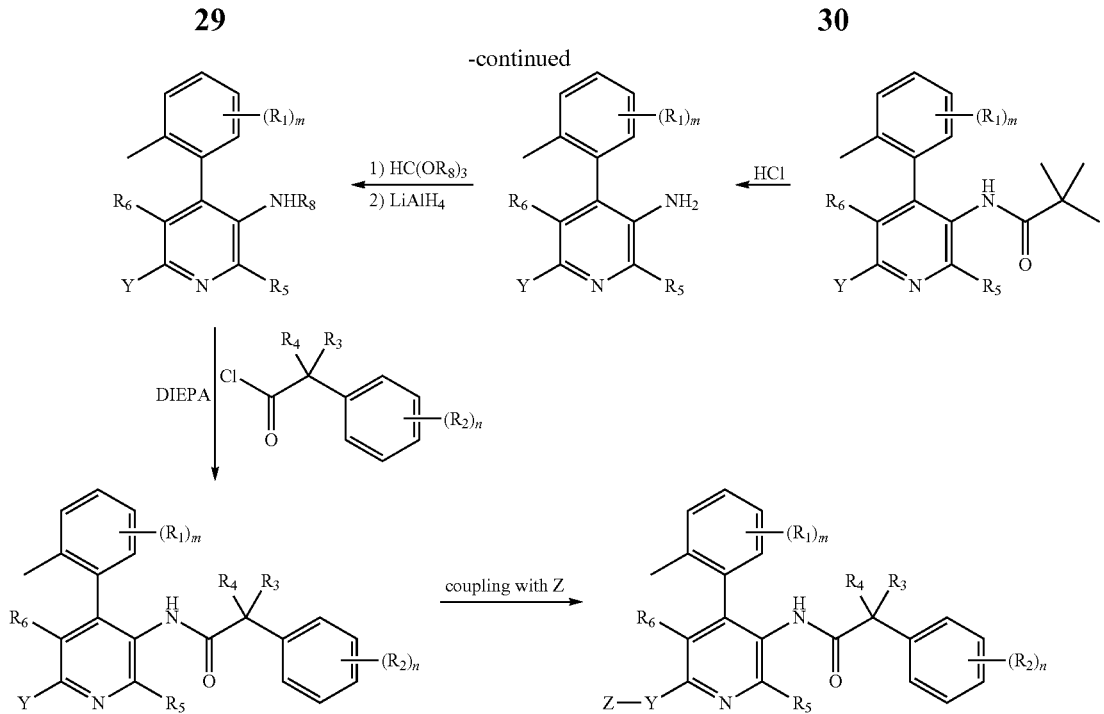

Other general procedures of preparing similar compounds to intermediate 1 of Scheme 1 are also disclosed in U.S. Pat. Nos. 6,303,790, 6,531,597, 6,297,375 and 6,479,483, which are referenced individually, specifically and in their entireties for the material contained in them that is relevant to the preparation of intermediate I.

Synthesis of methyl-[6-(4-methyl-piperazin-1-yl)-4-o-tolyl-pyridin-3-yl]-amine

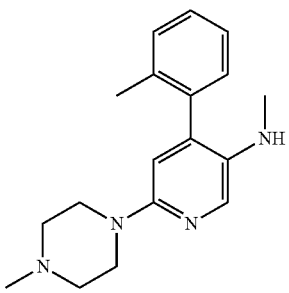

Step 1:

13.0 g (82.5 mMol) 6-Chloro-nicotinic acid in 65 ml THF were cooled to 0° C. and 206.3 ml (206.3 mMol) o-tolylmagnesium chloride solution (1M in THF) were added over 45 minutes. The solution obtained was further stirred 3 hours at 0° C. and overnight at room temperature. It was cooled to −60° C. and 103.8 ml (1.8 Mol) acetic acid were added, followed by 35 ml THF and 44.24 g (165 mMol) manganese (III) acetate dihydrate. After 30 minutes at −60° C. and one hour at room temperature, the reaction mixture was filtered and THF removed under reduced pressure. The residue was partitioned between water and dichloromethane and extracted. The crude product was filtered on silica gel (eluent: ethyl acetate/toluene/formic acid 20:75:5) then partitioned between 200 ml aqueous half-saturated sodium carbonate solution and 100 ml dichloromethane. The organic phase was washed with 50 ml aqueous half-saturated sodium carbonate solution. The combined aqueous phases were acidified with 25 ml aqueous HCl 25% and extracted with dichloromethane. The organic extracts were dried ($Na_2SO_4$) and concentrated under reduced pressure to yield 10.4 g (51%) of 6-chloro-4-o-tolyl-nicotinic acid as a yellow foam. MS (ISN): 246 (M−H, 100), 202 ($M-CO_2H$, 85), 166 (36).

Step 2:

To a solution of 8.0 g (32.3 mMol) 6-chloro-4-o-tolyl-nicotinic acid in 48.0 ml THF were added 3.1 ml (42.0 mMol) thionylchloride and 143 .mu.l (1.8 mMol) DMF. After 2 hours at 50° C., the reaction mixture was cooled to room temperature and added to a solution of 72.5 ml aqueous ammonium hydroxide 25% and 96 ml water cooled to 0° C. After 30 minutes at 0° C., THF was removed under reduced pressure and the aqueous layer was extracted with ethyl acetate. Removal of the solvent yielded 7.8 g (98%) 6-chloro-4-o-tolyl-nicotinamide as a beige crystalline foam. MS (ISP): 247 ($M+H^+$, 100).

Step 3:

1.0 g (4.05 mMol) 6-Chloro-4-o-tolyl-nicotinamide in 9.0 ml 1-methyl-piperazine was heated to 100° C. for 2 hours. The excess N-methyl-piperazine was removed under high vacuum and the residue was filtered on silica gel (eluent: dichloromethane) to yield 1.2 g (95%) 6-(4-methyl-piperazin-1-yl)-4-o-tolyl-nicotinamide as a light yellow crystalline foam.

MS (ISP): 311 ($M+H^+$, 100), 254 (62).

Step 4:

A solution of 0.2 g (0.6 mMol) 6-(4-methyl-piperazin-1-yl)-4-o-tolyl-nicotinamide in 1.0 ml methanol was added to a solution of 103 mg (2.6 mMol) sodium hydroxide in 1.47 ml (3.2 mMol) NaOCl (13%) and heated for 2 hours at 70° C. After removal of methanol, the aqueous layer was extracted with ethyl acetate. The combined organic extracts were dried ($Na_2SO_4$), concentrated under reduced pressure and the residue filtered on silica gel (eluent: dichloromethane/methanol 4:1) to yield 100 mg (70%) 6-(4-methyl-piperazin-1-yl)-4-o-tolyl-pyridin-3-ylamine as a brown resin. MS (ISP): 283 (M+H⁺, 100), 226 (42).

Step 5:

2.15 mil (11.6 mMol) Sodium methoxide in methanol were added over 30 minutes to a suspension of 0.85 g (4.6 mMol) N-bromosuccinimide in 5.0 ml dichloromethane cooled to −5° C. The reaction mixture was stirred 16 hours at −5° C. Still at this temperature, a solution of 1.0 g (3.1 mMol) 6-(4-methyl-piperazin-1-yl)-4-o-tolyl-nicotinamide in 5.0 ml methanol was added over 20 minutes and stirred for 5 hours. 7.1 ml (7.1 mMol) Aqueous HCl 1N and 20 ml dichloromethane were added. The phases were separated and the organic phase was washed with deionized water. The aqueous phases were extracted with dichloromethane, brought to pH=8 with aqueous NaOH 1N and further extracted with dichloromethane. The latter organic extracts were combined, dried (Na₂SO₄) and concentrated to yield 1.08 g (quant.) [6-(4-methyl-piperazin-1-yl)-4-o-tolyl-pyridin-3-yl]-carbamic acid methyl ester as a grey foam.

MS (ISP): 341 (M+H⁺, 100), 284 (35).

Step 6:

A solution of 0.5 g (1.4 mMol) [6-(4-methyl-piperazin-1-yl)-4-o-tolyl-pyridin-3-yl]-carbamic acid methyl ester in 3.0 ml dichloromethane was added over 10 minutes to a solution of 1.98 ml (6.9 mMol) Red-Al® (70% in toluene) and 2.5 ml toluene (exothermic, cool with a water bath to avoid temperature to go >50° C.). The reaction mixture was stirred 2 hours at 50° C. in CH₂Cl₂, extracted with ethyl acetate and cooled to 0° C. 4 ml Aqueous NaOH 1N were carefully (exothermic) added over 15 minutes, followed by 20 ml ethyl acetate. The phases were separated and the aqueous phase was extracted with ethyl acetate. The combined organic extracts were washed with deionized water and brine, dried (Na₂SO₄) and concentrated under reduced pressure to yield 0.37 g (89%) methyl-[6-(4-methyl-piperazin-1-yl)-4-o-tolyl-pyridin-3-yl]-amine as an orange resin. MS (ISP): 297 (M+H⁺, 100).

Synthesis of 2-(3,5-bis-Trifluoromethyl-phenyl)-2-methyl-propionyl Chloride

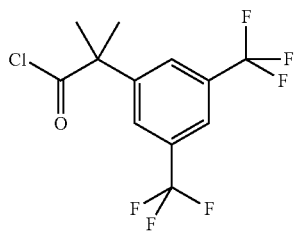 [SMILES: CC(C)(C(=O)Cl)c1cc(C(F)(F)F)cc(C(F)(F)F)c1]

15.0 g (50 mmol) 2-(3,5-bis-trifluoromethyl-phenyl)-2-methyl-propionic acid were dissolved in 127.5 ml dichloromethane in the presence of 0.75 ml DMF. 8.76 ml (2 eq.) Oxalyl chloride were added and after 4.5 hours, the solution was rotary evaporated to dryness. 9 ml Toluene were added and the resulting solution was again rotary evaporated, then dried under high vacuum yielding 16.25 g (quant.) of 2-(3,5-bis-trifluoromethyl-phenyl)-2-methyl-propionyl chloride as a yellow oil of 86% purity according to HPLC analysis. NMR (250 MHz, CDCl₃): 7.86 (br s, 1H); 7.77, (br s, 2H, 3H$_{arom}$); 1.77 (s, 6H, 2 CH₃).

Synthesis of 2-(3,5-bis(trifluoromethyl)phenyl)-N,2-dimethyl-N-(6-(4-methylpiperazin-1-yl)-4-(o-tolyl)pyridin-3-yl)propanamide (Netupitant)

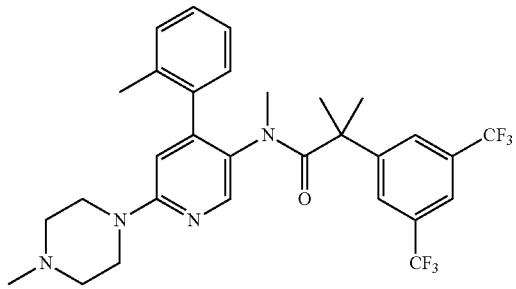 [SMILES: Cc1ccccc1-c1cc(N2CCN(C)CC2)ncc1N(C)C(=O)C(C)(C)c1cc(C(F)(F)F)cc(C(F)(F)F)c1]

A solution of 20 g (67.5 mmol) methyl-[6-(4-methyl-piperazin-1-yl)-4-o-tolyl-pyridin-3-yl]-amine and 17.5 ml (101 mmol) N-ethyldiisopropylamine in 200 ml dichloromethane was cooled in an ice bath and a solution of 24 g (75 mmol)₂-(3,5-bis-trifluoromethyl-phenyl)-2-methyl-propionyl chloride in 50 ml dichloromethane was added dropwise. The reaction mixture was warmed to 35-40° C. for 3 h, cooled to room temperature again and was stirred with 250 ml saturated sodium bicarbonate solution. The organic layer was separated and the aqueous phase was extracted with dichloromethane. The combined organic layers were dried (magnesium sulfate) and evaporated. The residue was purified by flash chromatography to give 31.6 g (81%) of 2-(3,5-bis(trifluoromethyl)phenyl)-N,2-dimethyl-N-(6-(4-methylpiperazin-1-yl)-4-(o-tolyl)pyridin-3-yl)propanamide as white crystals.

M.P. 155-157° C.; MS m/e (%): 579 (M+H⁺, 100).

Synthesis of 5-(2-(3,5-bis(trifluoromethyl)phenyl)-N,2-dimethylpropanamido)-2-(4-methylpiperazin-1-yl)-4-(o-tolyl)pyridine 1-oxide Scheme 2

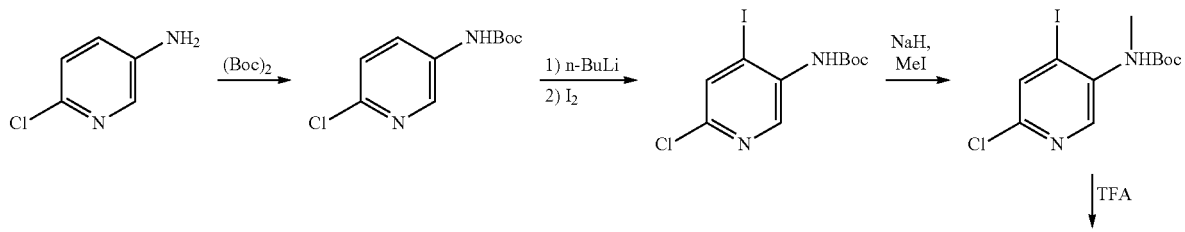

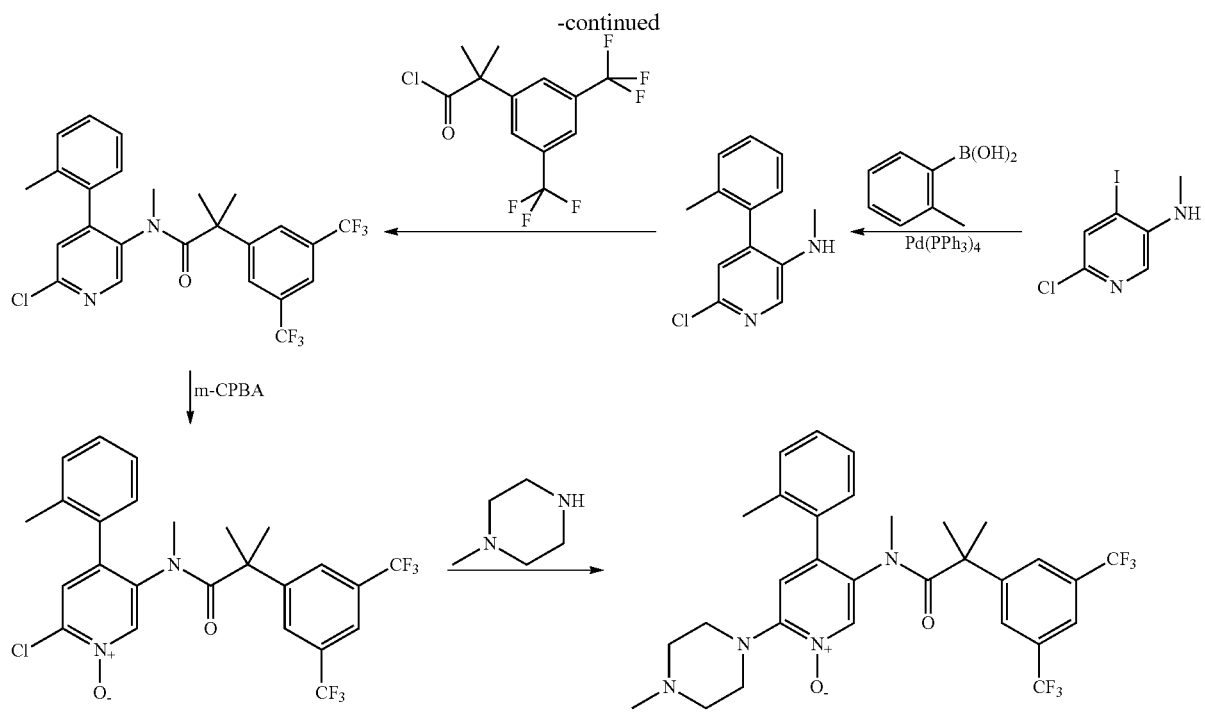

Step 1:
The solution of 6-chloropyridin-3-amine (115 g, 0.898 mol) and (Boc)₂O (215.4 g, 0.988 mol) in 900 mL of dioxane was refluxed overnight. The resulting solution was poured into 1500 mL of water. The resulting solid was collected, washed with water and re-crystallized from EtOAc to afford 160 g tert-butyl(6-chloropyridin-3-yl)carbamate as a white solid (Yield: 78.2%).

Step 2:
To the solution of tert-butyl(6-chloropyridin-3-yl)carbamate (160 g, 0.7 mol) in 1 L of anhydrous THF was added n-BuLi (600 mL, 1.5 mol) at −78° C. under N₂ atmosphere. After the addition was finished, the solution was stirred at −78° C. for 30 min, and the solution of I₂ (177.68 g, 0.7 mol) in 800 mL of anhydrous THF was added. Then the solution was stirred at −78° C. for 4 hrs. TLC indicated the reaction was over. Water was added for quench, and EtOAc was added to extract twice. The combined organic phases were washed with brine, dried over Na₂SO₄, filtered and purified by flash chromatography to afford 80 g of tert-butyl(6-chloro-4-iodopyridin-3-yl)carbamate as a yellow solid (32.3%).

Step 3:
To the solution of tert-butyl(6-chloro-4-iodopyridin-3-yl) carbamate (61 g, 0.172 mol) in 300 mL of anhydrous THF was added 60% NaH (7.6 g, 0.189 mol) at 0° C. under N₂ atmosphere. After the addition was finished, the solution was stirred for 30 min, and then the solution of MeI (26.92 g, 0.189 mol) in 100 mL of dry THF was added. Then the solution was stirred at 0° C. for 3 hrs. TLC indicated the reaction was over. Water was added for quench, and EtOAc was added to extract twice. The combined organic phases were washed with brine, dried over Na₂SO₄, filtered and concentrated to afford 63 g of crude tert-butyl(6-chloro-4-iodopyridin-3-yl)(methyl)carbamate used into the following de-protection without the further purification.

Step 4:
To the solution of tert-butyl(6-chloro-4-iodopyridin-3-yl)(methyl)carbamate (62.5 g, 0.172 mol) in 500 mL of anhydrous DCM was added 180 mL of TFA. Then the solution was stirred at room temperature for 4 hrs. Concentrated to remove the solvent, and purified by flash chromatography to afford 45.1 g 6-chloro-4-iodo-N-methylpyridin-3-amine as a yellow solid (Yield: 97.3%).

Step 5:
To the solution of 6-chloro-4-iodo-N-methylpyridin-3-amine (40.3 g, 0.15 mol) and 2-methylbenzene boric acid (24.5 g, 0.18 mol) in 600 mL of anhydrous toluene was added 400 mL of 2 N aq. Na₂CO₃ solution, Pd(OAc)₂ (3.36 g, 15 mmol) and PPh₃ (7.87 g, 0.03 mmol). The solution was stirred at 100° C. for 2 hrs. Cooled to room temperature, and diluted with water. EtOAc was added to extract twice. The combined organic phases were washed with water and brine consecutively, dried over Na₂SO₄, concentrated and purified by flash chromatography to afford 19 g 6-chloro-N-methyl-4-(o-tolyl)pyridin-3-amine as a white solid (Yield: 54.6%).

Step 6:
To the solution of 6-chloro-N-methyl-4-(o-tolyl)pyridin-3-amine (18.87 g, 81.3 mmol) and DMAP (29.8 g, 243.9 mmol) in 200 mL of anhydrous toluene was added the solution of 2-(3,5-bis-trifluoromethyl-phenyl)-2-methyl-propionyl chloride (28.5 g, 89.4 mmol) in toluene under N₂ atmosphere. The solution was heated at 120° C. for 23 hrs. Cooled to room temperature, poured into 1 L of 5% aq. NaHCO₃ solution, and extracted with EtOAc twice. The combined organic phases were washed by water and brine consecutively, dried over Na₂SO₄, filtered and purified by flash chromatography to afford 35 g 2-(3,5-bis(trifluoromethyl)phenyl)-N-(6-chloro-4-(o-tolyl)pyridin-3-yl)-N,2-dimethylpropanamide as a white solid (Yield: 83.9%).

Step 7:
To the solution of 2-(3,5-bis(trifluoromethyl)phenyl)-N-(6-chloro-4-(o-tolyl)pyridin-3-yl)-N,2-dimethylpropanamide (5.14 g, 10 mmol) in 60 mL of DCM was added m-CPBA (6.92 g, 40 mmol) at 0° C. under N₂ atmosphere. Then the solution was stirred overnight at room temperature.

1 N aq. NaOH solution was added to wash twice for removing the excess m-CPBA and a side product. The organic phase was washed by brine, dried over Na₂SO₄, filtered and concentrated to afford 5.11 g of crude 5-(2-(3,5-bis(trifluoromethyl)phenyl)-N,2-dimethylpropanamido)-2-chloro-4-(o-tolyl)pyridine 1-oxide as a white solid (Yield: 96.4%).

Step 8:

To the solution of crude 5-(2-(3,5-bis(trifluoromethyl)phenyl)-N,2-dimethylpropanamido)-2-chloro-4-(o-tolyl)pyridine 1-oxide (5.1 g, 9.62 mmol) in 80 mL of n-BuOH was added N-methylpiperazine (7.41 g, 74.1 mmol) under N₂ atmosphere. Then the solution was stirred at 80° C. overnight. Concentrated and purified by flash chromatography to afford 4.98 g 5-(2-(3,5-bis(trifluoromethyl)phenyl)-N,2-dimethylpropanamido)-2-(4-methylpiperazin-1-yl)-4-(o-tolyl)pyridine 1-oxide as a white solid (Yield: 87.2%). ¹HNMR (CDCl3, 400 MHz) δ 8.15 (s, 1H), 7.93 (s, 1H), 7.78 (s, 2H), 7.38 (m, 2H), 7.28 (m, 1H), 7.17 (m, 1H), 7.07 (s, 1H), 5.50 (s, 3H), 2.72 (d, J=4.4 Hz, 4H), 2.57 (m, 3H), 2.40 (s, 3H), 2.23 (s, 3H), 1.45~1.20 (m, 6H).

Synthesis of 4-(5-(2-(3,5-bis(trifluoromethyl)phenyl)-N,2-dimethylpropanamido)-1-oxido-4-(o-tolyl)pyridin-2-yl)-1-methylpiperazine 1-oxide

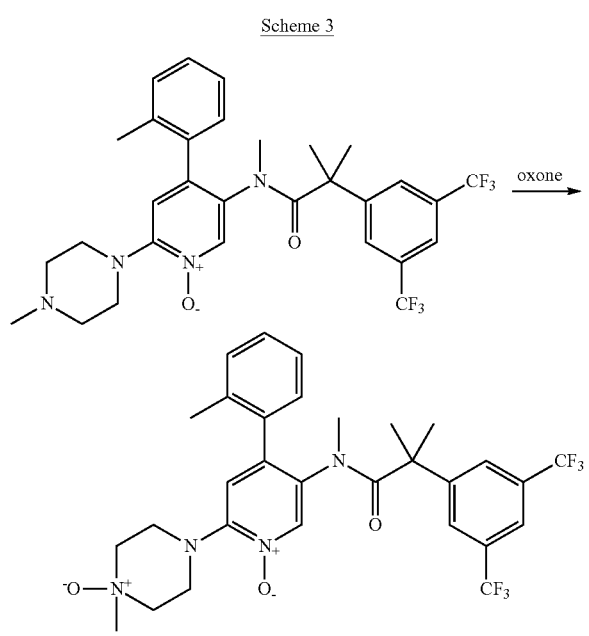

To a solution of 5-(2-(3,5-bis(trifluoromethyl)phenyl)-N,2-dimethylpropanamido)-2-(4-methylpiperazin-1-yl)-4-(o-tolyl)pyridine 1-oxide (3 g, 5.05 mmol) and NaHCO₃ (0.354 g, 12.66 mmol) in 60 mL of MeOH and 15 mL of H₂O were added potassium monopersulfate triple salt (1.62 g, 26.25 mmol) at room temperature during 15 min. After stirring for 4 hrs at room temperature under N₂ atmosphere, the reaction mixture was concentrated in vacuo and purified by flash chromatography (eluent: MeOH). The product was dissolved into DCM, the formed solid was filtered off, and the solution was concentrated under reduced pressure to afford 1.77 g 4-(5-(2-(3,5-bis(trifluoromethyl)phenyl)-N,2-dimethylpropanamido)-1-oxido-4-(o-tolyl)pyridin-2-yl)-1-methylpiperazine 1-oxide as a white solid (Yield: 57.4%). ¹HNMR (CDCl3, 400 MHz) δ 8.06 (s, 1H), 7.78 (s, 1H), 7.60 (s, 2H), 7.37~7.20 (m, 4H), 6.81 (s, 1H), 3.89 (s, 21H), 3.74 (m, 4H), 3.31 (m, 5H), 2.48 (s, 3H), 2.18 (s, 3H), 1.36 (s, 6H).

Synthesis of 1-(5-(2-(3,5-bis(trifluoromethyl)phenyl)-N,2-dimethylpropanamido)-4-(o-tolyl)pyridin-2-yl)-4-methylpiperazine 1,4-dioxide

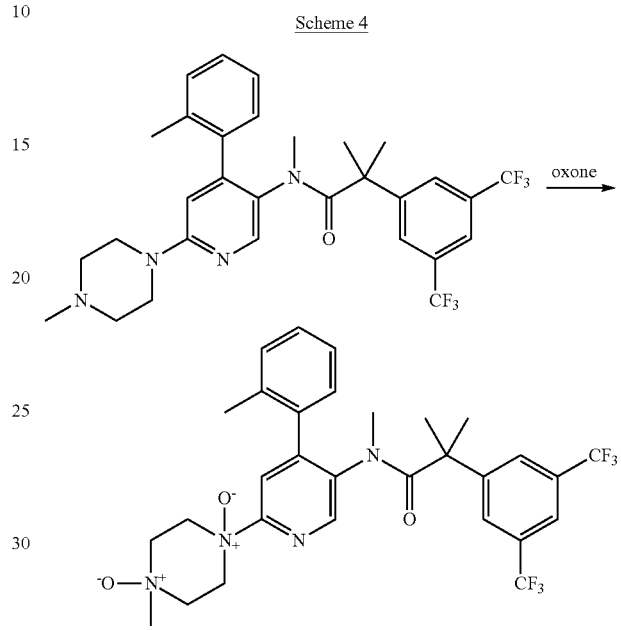

To the solution of 2-(3,5-bis(trifluoromethyl)phenyl)-N,2-dimethyl-N-(6-(4-methylpiperazin-1-yl)-4-(o-tolyl)pyridin-3-yl)propanamide (11.1 g, 19.2 mmol) in 75 ml of Methanol was added sodium bicarbonate (3.38 g, 40.3 mmol) dissolved in 20 ml of water. Then Oxone (14.75 g, 48.0 mmol) was added to the stirred solution at room temperature in 3-4 portions. The suspension was heated for 4 h at 50° C. After filtration of the salts (washed with 3×8 ml of methanol), the solvent has been evaporated under reduced pressure and substituted by DCM (30 ml). The organic phase was washed with water (5×30 ml), dried over Na₂SO₄, filtered, concentrated and purified by precipitation in toluene to afford 9.3 g 1-(5-(2-(3,5-bis(trifluoromethyl)phenyl)-N,2-dimethylpropanamido)-4-(o-tolyl)pyridin-2-yl)-4-methylpiperazine 1,4-dioxide as a white solid (Yield: 80%). ¹H-NMR (CDCl3, 400 MHz, at 333K) δ 8.27 (s, 2H), 7.75 (s, 1H), 7.63 (s, 2H), 7.26~7.19 (m, 2H), 7.14 (t, 1H, J=7.4 Hz), 7.09 (d, 1H, J=7.4 Hz), 4.93 (t, 2H, J=11.6 Hz), 4.70 (t, 2H, J=11.6 Hz), 4.12 (d, 2H, J=10.7 Hz), 3.84 (s, 3H), 3.50 (d, 2H, J=10.3 Hz), 2.47 (s, 3H), 2.12 (s, 3H), 1.40 (s, 6H).

Synthesis (A) of di-tert-butyl(chloromethyl)phosphate

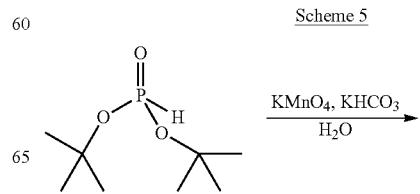

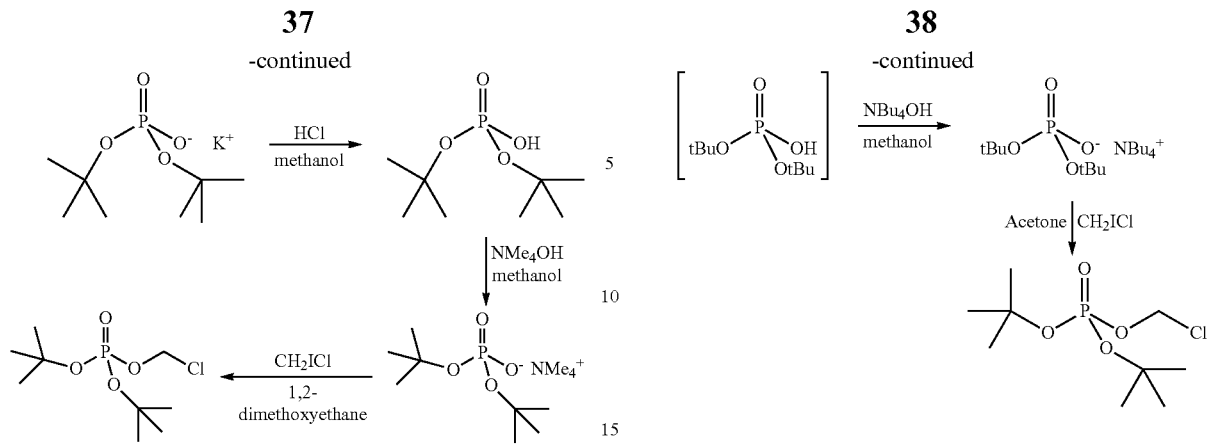

Di-tert-butyl phosphohite (40.36 mmole) was combined with potassium bicarbonate (24.22 mmole) in 35 ml of water. The solution was stirred in an ice bath and potassium permanganate (28.25 mmole) was added in three equal portions over one hour's time. The reaction as then allowed to continue at room temperature for an additional half hour.

Decolorizing carbon (600 mg) was then incorporated as the reaction was heated to 60° C. for 15 minutes. The reaction was then vacuum filtered to remove solid magnesium dioxide. The solid was washed several times with water. The filtrate was then combined with one gram of decolorizing carbon and heated at 60° C. for an additional twenty minutes. The solution was again filtered to yield a colorless solution, which was then evaporated under vacuum to afford crude Di-tert-butyl phosphate potassium salt. Di-tert-butyl phosphate potassium salt (5 g, 20.14 mmole) was dissolved in methanol (15 g): to this solution at 0° C. a slight excess of concentrated HCl is slowly added with efficient stirring at 0° C. The addition of acid causes the precipitation of potassium chloride. The solid is then filtered and washed with methanol. The compound in the mother liquor is then converted to the ammonium form by adding an equal molar amount of tetramethylammonium hydroxide (3.65 g, 20.14 mmole) while keeping the reaction cooled by a salt/ice bath with efficient stirring. The resulting clear solution is placed under reduced pressure to give the crude product. To the tetramethylammonium di-tert-butyl-phosphate dissolved in refluxing dimethoxyethane is then added 4.3 grams of chloroiodomethane (24.16 mmole) and stirred for 1-2 hours. The reaction is then filtered and the filtrate is placed under reduced pressure to concentrate the solution in DME. The chloromethyl di-tert-butyl phosphate 12-16% in DME is used in the synthesis of 4-(5-(2-(3,5-bis (trifluoromethyl)phenyl)-N,2-dimethylpropanamido)-4-(o-tolyl)pyridin-2-yl)-1-methyl-1-((phosphonooxy)methyl) piperazin-1-ium without further purifications (60% yield): $^1H$NMR (CD$_3$OD, 300 MHz) δ 1.51 (s, 12H), 5.63 (d, 2H, J=14.8). $^{31}$P-NMR (CD$_3$OD, 300 MHz) δ −11.3 (s, 1P).

Synthesis (B) of
di-tert-butyl(chloromethyl)phosphate

Scheme 5A

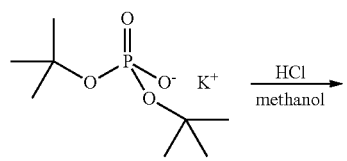

Di-tert-butyl phosphate potassium salt (5 g, 20.14 mmole) is dissolved in methanol (15 g): to this solution at 0° C. a slight excess of concentrated HCl is slowly added with efficient stirring at 0° C. The addition of acid causes the precipitation of potassium chloride. The solid is then filtered and washed with methanol. The compound in the mother liquor is then converted to the ammonium form by adding an equal molar amount of tetrabuthylammonium hydroxide 1 M in methanol (20.14 mmole) while keeping the reaction cooled at 0° C. with efficient stirring. The resulting clear solution is placed under reduced pressure to give the intermediate product. The tetrabuthylammonium di-tert-butyl-phosphate dissolved in acetone is then added dropwise to 53.3 grams of chloroiodomethane (302.1 mmole) and stirred at 40° C. for 1-2 hours. The solvent and excess of chloroiodomethane are distilled off, the reaction mass suspended in TBME and then filtered. The filtrate is washed by a saturated solution of sodium bicarbonate and water and then placed under reduced pressure to substitute the solvent by acetone, i.e., to remove the solvent after which it is replaced with acetone. The chloromethyl di-tert-butyl phosphate 7-20% in acetone is used in the next step without further purifications (70-80% yield): $^1$H-NMR (CD$_3$OD, 300 MHz) δ 1.51 (s, 12H), 5.63 (d, 2H, J=14.8). $^{31}$P-NMR (CD$_3$OD, 300 MHz) δ −11.3 (s, 1P).

Stability studies of 4-(5-(2-(3,5-bis(trifluoromethyl) phenyl)-N,2-dimethylpropanamido)-4-(o-tolyl)pyridin-2-yl)-1-methyl-1-((phosphonooxy)methyl)piperazin-1-ium salts In order to further improve the stability and solubility of 4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium, a variety of its derivative salts were synthesized and tested. Their synthesis employed either a) neutralization of the dried diacid phosphate species and its corresponding base salts or b) a direct acid deprotection starting from the dried di(tert-butyl)-protected phosphate species. Neutralization was performed with L-histidine, magnesium salt, N-methyl-D-glucamine (dimeglumine), and L-lysine. Both procedures were tried in the synthesis of citric derivatives whereas with other acids the direct deprotection reaction was used. The figures below show the most relevant structures.

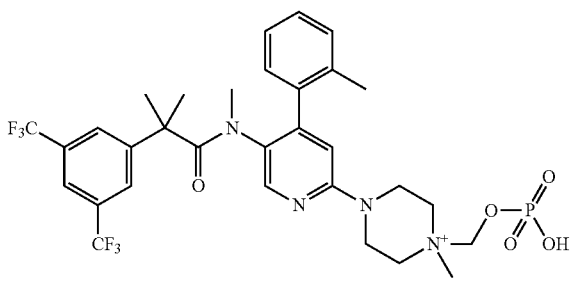

Parent acid species

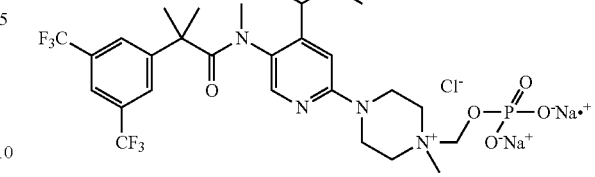

Dibasic phosphate species

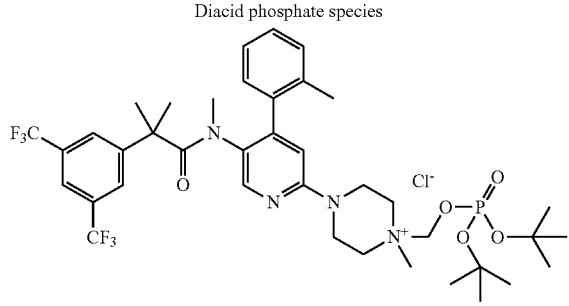

Diacid phosphate species

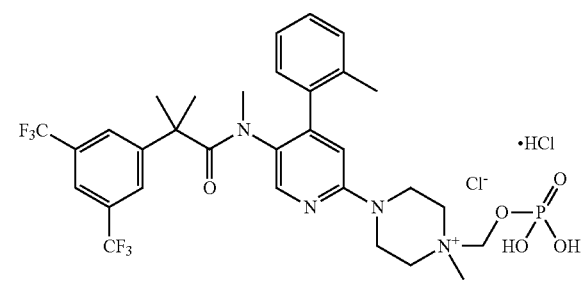

Chloride hydrochloride species

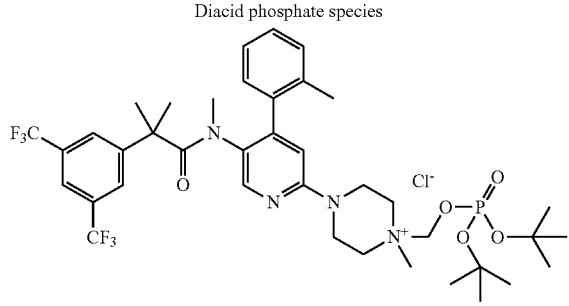

Protected phosphate species

When the parent acid species was not stored in dry condition it was found to undergo over 8% degradation in the first week and over 65% degradation in the first six months. When the dried parent acid species was held at 30° C. in air it underwent 0.05% degradation in the first 7 days and at total of 7.03% degradation in six months. When the dried parent acid species was held under argon at room temperature it underwent up to 0.13% degradation in the first 7 days but then was essentially stable for six months. Results for various derivative salts are shown in Table 1 below.

TABLE 1

Representative Degradation Results for Salts

| Solvents | Additives | Yield % | Purity A % HPLC | Comments |
|---|---|---|---|---|
| MeOH | L-Histidine, 2 eq. | 26.6% | 95.94% | Degradation: +0.70% in 6 days (in air) +0.46% in 6 days (in argon) |
| MeOH | Mg(OH)$_2$, 2 eq. | 48.6% | 94.11% | Degradation: +0.81% in 6 days (in air) +0.29% in 6 days (in argon) |
| MeOH + DCM, 1:1 | Citric acid, 2 eq. | N.A. | 94.40% | From protected species. |
| MeOH | 1. HCl dioxane, 4 eq. 2. Ca(OH)$_2$ | >90% | 94.50% | From protected species. |
| MeOH | H$_3$PO$_4$, 85%, 2 eq. | >90% | 98.81% | From protected species and retains 0.39% of that species. |
| MeOH | HBr, 48%, 4 eq. | 84.6% | 96.11% | From protected species. Product degrades rapidly. |
| MeOH + DCM, 1:4 | CH$_3$SO$_3$H | N.A. | 61.54% | From protected species. Product NOT stable: contains 32.45% decomposition species. |
| MeOH | NaH$_2$PO$_4$, 4 eq. | N.A. | n.d. | Only 1.27 of parent species formed. Poor reaction. |
| MeOH | N-methyl-D-glucamine (Meglumine), 2 eq. | N.A. | 96.88% | Degradation: +0.87% in 6 days (in air) +1.52% in 11 days (in argon) |
| MeOH | N-methyl-D-glucamine (Meglumine), 1 eq. | >99% | 97.42% | Degradation: +0.77% in 6 days (in air) +0.83% in 7 days (in argon) |

TABLE 1-continued

Representative Degradation Results for Salts

| Solvents | Additives | Yield % | Purity A % HPLC | Comments |
|---|---|---|---|---|
| MeOH+ DCM, 5:2 | 1. NaOH, 3 eq 2. Citric acid, 1 eq. | 96.5% | 97.49% | Degradation: +0.09% in 2 days (in argon) +0.59% in 89 days (in argon) |
| MeOH+ DCM, 5:2 | 1. NaOH, 3 eq. 2. Fumaric acid, 1 eq. | 93.8% | 97.46% | Degradation: +1.95% in 14 days (in air) +1.80% in 12 days (in argon) |
| MeOH | L-lysine, 1 eq. | >99% | 97.62% | Degradation: +0.69% in 14 days (in air) +0.48% in 12 days (in argon) |

A more comprehensive showing of stability results is given in FIG. 1, where the horizontal axis represents number of days of testing and the vertical axis represents the mass percent of degradation. Alphabetical letters are used to denote data points on the graph that correspond to degradation percentage values over time for respective salts of the same parent compound as just described above and in Table 2 below. The drawn lines correspond to general trends over periods of days for the benchmark salt (the disodium salt) and for the few salts that manifested more desirable results than the disodium salt.

TABLE 2

Identity Codes for Salts and Gases in FIG. 1.

| Letter Code | Salt | Ambient gas for storage |
|---|---|---|
| a | 2 Dimeglumine | Air |
| b | 2 Dimeglumine | Argon |
| c | Dimeglumine | Air |
| d | Dimeglumine | Argon |
| e | Lysine | Air |
| f | Lysine | Argon |
| g | Fumarate | Air |
| h | Fumarate | Argon |
| i | Citrate | Air |
| j | Citrate | Argon |
| k | Bromide | Air |
| l | Bromide | Argon |
| m | Mesylate | Nitrogen |
| n | Phosphate | Air |
| o | Phosphate | Argon |
| p | Citrate | Nitrogen |
| q | Calcium | Air |
| r | Calcium | Argon |
| s | Chloride hydrochloride, anhydrous | Air |
| t | Chloride hydrochloride, anhydrous | Argon |
| u | Disodium Salt | Air |
| v | Histidine | Air |
| w | Histidine | Argon |
| x | Magnesium | Air |
| y | Magnesium | Argon |

Synthesis (A) of 4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium chloride hydrochloride Scheme 6

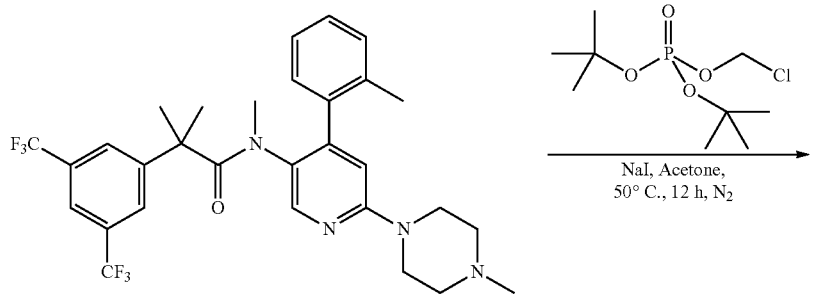

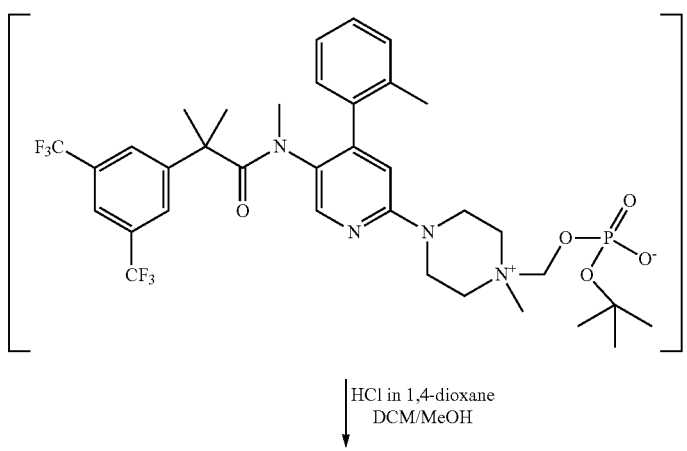

HCl in 1,4-dioxane
DCM/MeOH

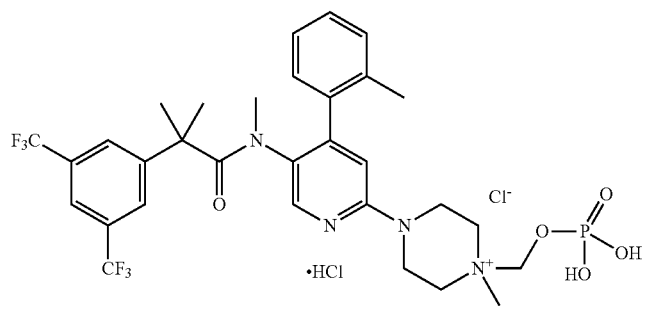

The solution of chloromethyl di-tert-butyl phosphate in DME (250 g from a 10% solution, 96.64 mmole) was evaporated under reduced pressure until the formation of pale yellow oil, dissolved then at 50° C. with 318 ml of Acetonitrile. 17.2 g (80.54 mmole) of 1,8-bis(dimethylamino)naphtalene and 46.6 g (80.54 mmole) of 2-(3,5-bis(trifluoromethyl)phenyl)-N,2-dimethyl-N-(6-(4-methylpiperazin-1-yl)-4-(o-tolyl)pyridin-3-yl)propanamide were added and the solution heated at 90° C. for at least 12 h. After the addition of 75 g of isopropylether, the precipitated crude product was cooled at room temperature, filtered and washed with acetonitrile, isopropylether/acetone, 3:1 and isopropylether, and dried under reduced pressure to afford 20-33 g of the 4-(5-{2-[3,5-bis(trifluoromethyl)phenyl]-N,2-dimethylpropanamido}-4-(o-tolyl)pyridin-2-yl)-1-methyl-1-{[(tert-butoxy)phosphoryl]oxymethyl}piperazin-1-ium as white solid (Yield: 30-50%). $^1$H-NMR (CD$_3$OD, 400 MHz) δ 7.98 (s, 1H), 7.86 (s, 1H), 7.76 (s, 2H), 7.33-7.10 (m, 4H), 6.80 (s, 1H), 5.03 (d, 2H, J$_{PH}$=8.5 Hz), 4.52 (s, 2H), 4.13 (m, 2H), 3.83 (m, 2H), 3.69 (m, 2H), 3.52 (m. 2H), 3.23 (s, 3H), 2.53 (s, 3H), 2.18 (s, 3H), 1.46 (s, 18H), 1.39 (s, 6H). $^{31}$P-NMR (CD$_3$OD, 161 MHz) δ −5.01 (s, 1P). To 20 g (23.89 mmole) of the 4-(5-{2-[3,5-bis(trifluoromethyl)phenyl]-N,2-dimethylpropanamido}-4-(o-tolyl)pyridin-2-yl)-1-methyl-1-{[(tert-butoxy)phosphoryl]oxymethyl}piperazin-1-ium dissolved in 180 g of methanol and 400 g of dichloromethane was added HCl 4M in dioxane (18.8 g, 71.66 mmole) and the solution was heated for 3 h at reflux. After the addition of 200 g of dioxane, DCM and methanol were distilled under reduced pressure until precipitation of the product, which was filtered and washed with isopropylether (100 g), acetone (30 g) and pentane (2×60 g). The product was finally dried under reduced pressure at 55° C. to afford 15-17 g of 4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium chloride hydrochloride as white solid (Yield: 88-93%). $^1$H-NMR (CD$_3$OD, 400 MHz) δ 7.02 (s, 1H), 7.87 (s, 1H), 7.74 (s, 2H), 7.33-7.40 (m, 2H), 7.27 (m, 1H), 7.21 (s, 1H), 7.16 (d, 1H, J=8.2 Hz), 5.27 (d, 2H, J$_{PH}$=7.9 Hz), 4.29 (m, 2H), 4.05 (m, 2H), 3.85 (m, 2H), 3.74 (m, 2H), 3.35 (s, 3H), 2.62 (s, 3H), 2.23 (s, 3H), 1.38 (s, 6H). $^{31}$P-NMR (CD$_3$OD, 161 MHz) δ −2.81 (t, 1P, J$_{PH}$=7.9 Hz).

Synthesis (B) of 4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium chloride hydrochloride

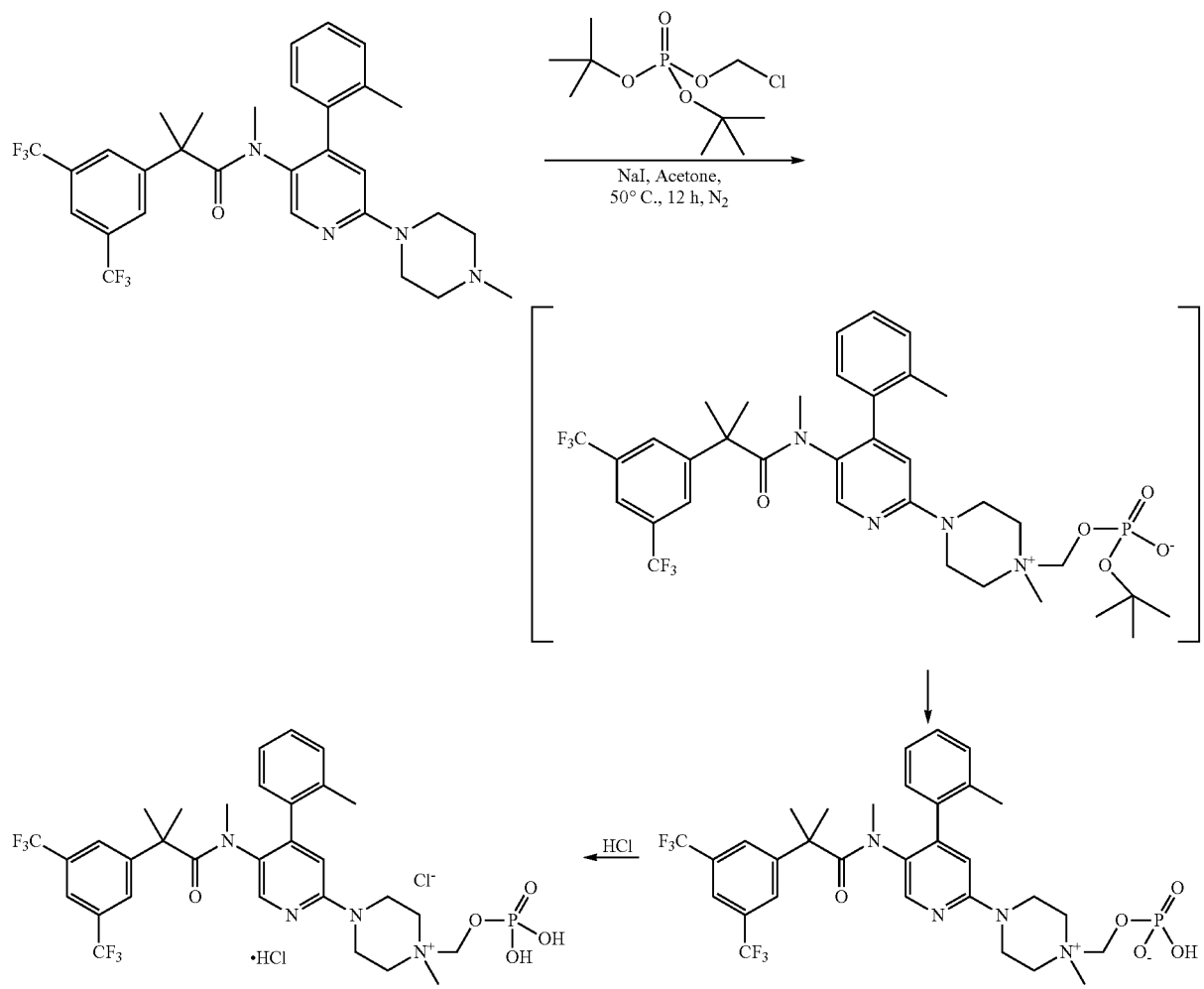

Scheme 6A

To the solution of chloromethyl di-tert-butyl phosphate in Acetone (22.1 g from a 10% solution, 85.58 mmole), 15.5 g (103.24 mmole) of sodium iodide and 33.0 g (57.00 mmole) of netupitant were added and the solution heated at 50° C. for at 6-16 h. The precipitated salts were filtered off, the acetone distilled under reduced pressure and the crude product dissolved in 43.0 g of methanol and 43.0 g 1,4-dioxane. 12.6 g of HCl 4M in dioxane (113.85 mmole) were added, and then methanol is distilled off at 40° C. under reduced pressure. The solution is cooled at 5° C. and stirred at 5° C. for at least 2 h at 5° C. The product was isolated by filtration, purified by additional slurry in acetone (238 g), and filtered and washed with acetone (47 g) and pentane (2×72 g).

The product was finally dried under reduced pressure at 60° C. to afford 22-30 g of white-yellowish solid (Yield: 50-70%)

$^1$H-NMR (CD$_3$OD, 400 MHz) δ 7.02 (s, 1H), 7.87 (s, 1H), 7.74 (s, 2H), 7.33-7.40 (m, 2H), 7.27 (m, 1H), 7.21 (s, 1H), 7.16 (d, 1H, J=8.2 Hz), 5.27 (d, 2H, J$_{PH}$=7.9 Hz), 4.29 (m, 2H), 4.05 (m, 2H), 3.85 (m, 2H), 3.74 (m, 2H), 3.35 (s, 3H), 2.62 (s, 3H), 2.23 (s, 3H), 1.38 (s, 6H). $^{31}$P-NMR (CD$_3$OD, 161 MHz) δ −2.81 (t, 1P, J$_{PH}$=7.9 Hz).

It is to be understood that the product shown in Scheme 6.A is illustrative, being just one of several permutations in which the acidic protons bond to various atoms in an equilibrium. For instance depiction of other permutations would show a proton bound to one or more of the N atoms while one or more of the O atoms bound to the P atom would bear an anionic charge. The invention comprises all of the molecular species within that equilibrium and the product shown in the FIGURE is intended to represent all of them in a generic fashion.

7. Evaluation of Representative Compounds of Formula (I)

i. Chemical Stability and Solubility

The chemical stability and aqueous solubility of some representative compounds of Formula (I), compared to some reference compounds, are reproduced in Table 3 below. Stability was tested according to ICH guidelines under accelerated conditions (40° C.).

TABLE 3

Chemical Stability and Solubility of Representative Compounds

| Compound No. | Compound Structure | Chemical Stability | Solubility (neutral pH) |
|---|---|---|---|
| 1 | 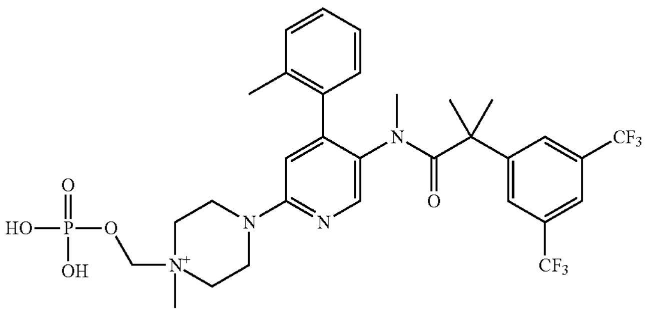 [SMILES: Cc1ccccc1-c1cc(N2CC[N+](C)(COP(=O)(O)O)CC2)ncc1N(C)C(=O)C(C)(C)c1cc(C(F)(F)F)cc(C(F)(F)F)c1] | medium | 10-15 mg/ml |
| 2 | 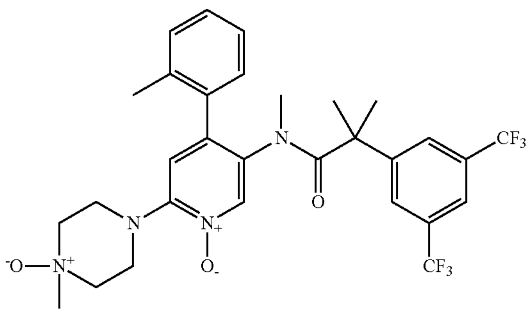 | high | >10 mg/ml |
| 3 | 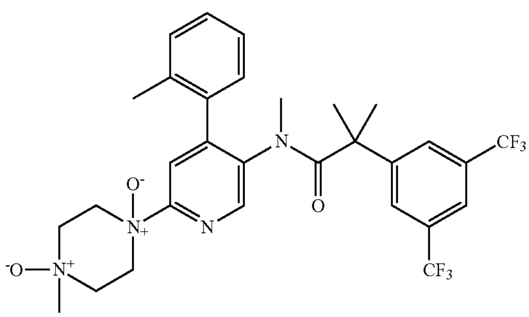 | high | >10 mg/ml |
| 4 | 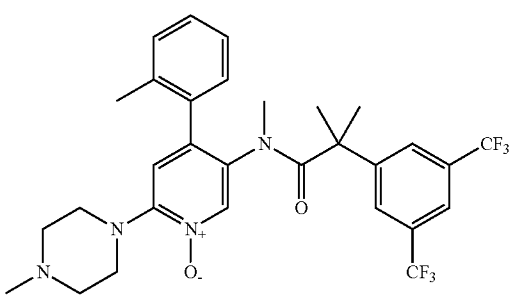 | medium | ~0.6 mg/ml |
| 5* | 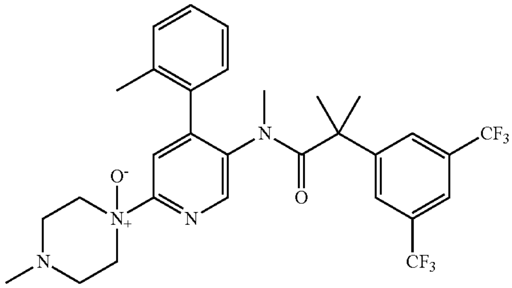 [SMILES: Cc1ccccc1-c1cc([N+]2([O-])CCN(C)CC2)ncc1N(C)C(=O)C(C)(C)c1cc(C(F)(F)F)cc(C(F)(F)F)c1] | medium | ~1 mg/ml |

TABLE 3-continued

Chemical Stability and Solubility of Representative Compounds

| Compound No. | Compound Structure | Chemical Stability | Solubility (neutral pH) |
|---|---|---|---|
| 6 | 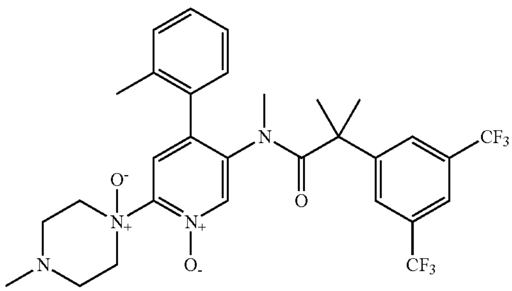 | low | N/A |
| 7 | 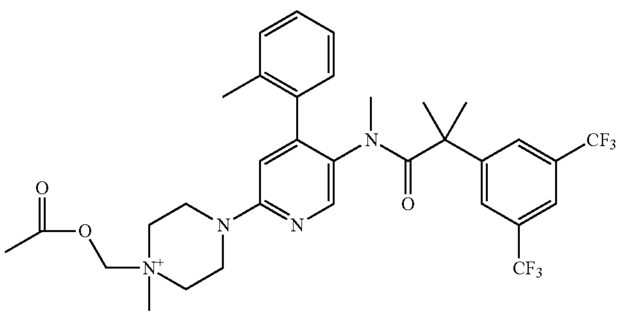 [SMILES: CC(=O)OC[N+]1(C)CCN(c2cc(-c3ccccc3C)c(N(C)C(=O)C(C)(C)c3cc(C(F)(F)F)cc(C(F)(F)F)c3)cn2)CC1] | low | insoluble |
| 8 | 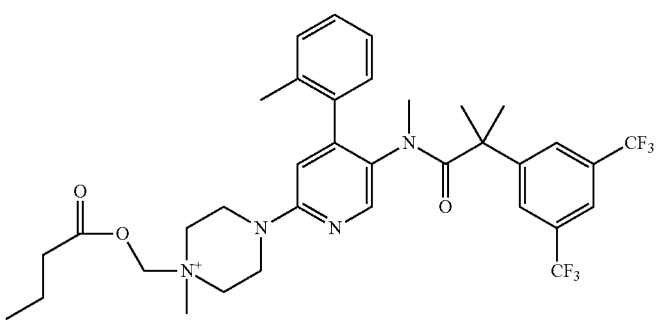 [SMILES: CCCC(=O)OC[N+]1(C)CCN(c2cc(-c3ccccc3C)c(N(C)C(=O)C(C)(C)c3cc(C(F)(F)F)cc(C(F)(F)F)c3)cn2)CC1] | Low | insoluble |
| 9* | 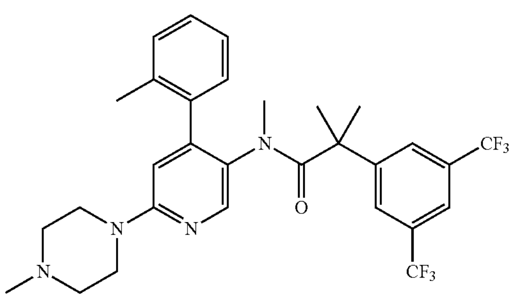 [SMILES: Cc1ccccc1-c1cc(N2CCN(C)CC2)ncc1N(C)C(=O)C(C)(C)c1cc(C(F)(F)F)cc(C(F)(F)F)c1] | | 0.25 |

*Reference Compound ii. Local Tolerance

In contrast to netupitant (compound no. 9 in the above table), seven-day local tolerability study of three compounds (e.g., compound nos. 1-3 of the above Table 1) on rat was conducted. All three compounds exhibited good local tolerability which is demonstrated by the below findings:
- There were minimal signs of inflammation at injection site and there was little edema;
- No later stage thrombus was found in any animal studied;
- Severity of inflammation was similar in compound and vehicle-treated animals;
- No tissue necrosis was observed in any of the tails; and
- The inflammation and palethrombus were caused by the needle injection through blood vessels.

iii. Pharmacokinetic Studies

The pharmacokinetics (PKs) study of three compounds (e.g., compound nos. 1-3 of the above Table 3), as compared to a reference compound—netupitant (orally administered), on rat and dog was conducted.

Rat PKs Study: The rats tested in the study were Wistar rats, male, body weight 220-240 g, and 5 rats per group. The dose was 10 mg/kg administered by intravenous (IV) slow bolus injection into the tail vein at a rate of 1 ml/min. The dose was administered to each animal at a dose volume of 5 ml/kg (the pre-formulation is 5% Glucose solution). Control animals received the vehicle alone. The dose was administered to each animal on the basis of the most recently recorded body weight and the volume administered was recorded for each animal. Before administration, rats were fasted 12 hr, water ad libitum. After 240 min time point blood was collected, rats were fed. 0.2-0.3 ml blood was collected in tubes contained EDTA/NaF as anticoagulant and stabilizer at pre-dose and at 0.05, 0.25, 0.5, 1, 2, 4, 6, 8, 24 and 48 hrs after intravenous administration. After centrifugation, plasma was removed and stored deep-frozen approximately −20° C. until analysis. Prepared quantification standard curve at 2, 10, 40, 100, 200, 1000 and 2000 ng/ml (diluted from methanol stock with methanol containing 1% formic acid). Aliquot 50 ul of standard solution and spiked into 50 ul of blank rat plasma samples either for standard curve or for QC samples, followed by adding 100 ul of acetonitrile (with IS). 50 ul of methanol replaced the compound standard methanol solution was used to spike 50 ul of rat plasma samples, and added 100 ul of acetonitrile (with IS), for the determination of rat plasma samples. Plasma samples of time points 3, 15 and 30 min after intravenous administration were diluted 10 or 5 fold with blank rat plasma, respectively. Plasma was pre-prepared with acetonitrile using protein precipitate (PPP). Rat plasma samples were analyzed by using an API4000 MS coupled with HPLC. Repaglinide was used as internal standard. Using an internal calibration method for compound 1 of the above Table 1 or Netupitant quantitation, the LLOQ and the linear range of standard curve were 2 ng/ml and 2-2000 ng/ml, respectively.

Dog PKs Study: the dogs tested in the study were Beagle dogs, body weight 8-10 kg, and 3 male dogs per group. The four PK experiments were performed in 12 naïve dogs. The dose was 3 mg/kg administered via intravenous (IV) slow injection into the left and right cephalic or left and right saphenous veins used in rotation. The dose volume was 2 ml/kg in glucose 5% v/v solution at a fixed injection rate of 4 ml/min using an infusion pump (KDS 220, KD Scientific). The dose was administered to each animal on the basis of the most recently recorded body weight and the volume administered was recorded for each animal. Netupitant 3 mg/kg dose was tested at 2 ml/kg in vehicle (DMSO:Ethanol: Tween80 solution=5:4:1:90, v/v), dependence on its solubility. Dose was freshly prepared before each single PK experiment. Before administration, dogs were fasted 12 hr, water ad libitum. After 480 min time point blood was collected, dogs were fed. 0.5 ml blood was collected in heparinised tubes at pre-dose and at 2, 5, 15, 30 min, 1, 2, 4, 6, 8, 12, 24, 36, 48 and 72 hr after intravenous administration. Plasma samples would be kept at −20 degree till analysis. After 2 weeks washout, the same group (IV for Netupitant) was dosed Netupitant 3 mg/kg by gavage administration, the dose volume was 4 ml/kg in vehicle (Hypromellose 0.5%, Tween-80 0.1%, Sodium Chloride 0.9% in distilled water). Prepared quantification standard curve at 2, 10, 40, 100, 200, 1000 and 2000 ng/ml (diluted from methanol stock with methanol containing 1% formic acid). Aliquot 50 ul of standard solution and spiked into 50 ul of blank dog plasma samples either for standard curve or for QC samples, followed by adding 100 ul of acetonitrile (with IS). 50 ul of methanol replaced the compound standard methanol solution was used to spike 50 ul of dog plasma samples, and added 100 ul of acetonitrile (with IS), for the determination of dog plasma samples. Plasma samples of time points 2, 5, and 30 min after intravenous administration were diluted 5 or 2 folds with blank dog plasma, respectively. Plasma was pre-prepared with acetonitrile using protein precipitate (PPP). Dog plasma samples were analyzed by using an API4000 MS coupled with HPLC. MRM(+) was used to scan for Netupitant and compound nos. 1-3 of the above Table 3, respectively. Repaglinide was used as internal standard.

It was found that all three compounds, when intravenously administered at a dosage of 3 mg/kg, were efficiently converted to netupitant in rats and dogs. It was also found that compound no. 1 is bioequivalent to oral netupitant at the same dose in dog. The data of the comparative bioequivalence study is reproduced in below Table 4:

TABLE 4

Comparative Bioequivalence Studies of Netupitant and Related Compounds

| | IV | | | PO |
|---|---|---|---|---|
| | Compound 1 | Compound 2 | Compound 3 | Netupitant* |
| Dose (mg/kg) | 3 | 3 | 3 | 3 |
| Dose (mg/kg, equivalent to netupitant) | 2.31 | 2.84 | 2.84 | 3 |
| Mean AUC$_{0-t}$ (ng · min/ml) | 315627 | 88732 | 192730 | 307285 |
| Bioequivalence (%) | 103 | 29 | 63 | |

*Reference Compound

Throughout this application, various publications are referenced. The disclosures of these publications in their entireties are hereby referenced individually and specifically for the material contained in them that is discussed in the sentence in which the reference is relied upon. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pharmaceutically acceptable salt of a compound of formula GA1:

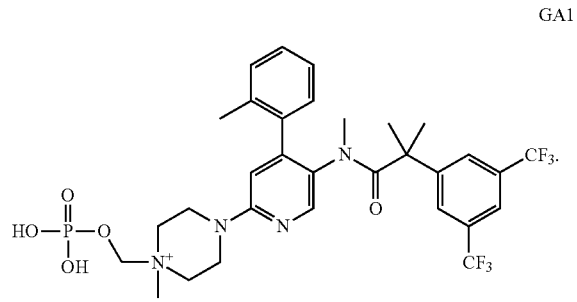 [SMILES: Cc1ccccc1-c1cc(N2CC[N+](C)(COP(=O)(O)O)CC2)ncc1N(C)C(=O)C(C)(C)c1cc(C(F)(F)F)cc(C(F)(F)F)c1]

2. A method of treating emesis, bladder dysfunction, depression or anxiety in a patient, comprising administering to said patient in need thereof a therapeutically effective amount of a compound of formula GA1:

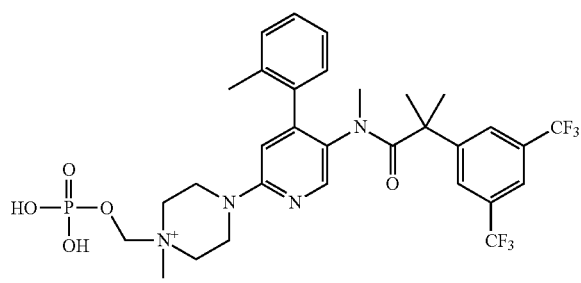

or a pharmaceutically acceptable salt thereof.

3. The method of claim 2, wherein the patient is a human.

4. The method of claim 2, wherein said compound, or pharmaceutically acceptable salt thereof, is intravenously administered at a dosage of from 10 mg to 200 mg.

5. The method of claim 2, wherein said emesis comprises chemotherapy induced nausea and vomiting, radiation therapy induced nausea and vomiting, or post-operative nausea and vomiting.

6. The method of claim 2, wherein said emesis is induced by moderately or highly emetogenic chemotherapy.

7. The method of claim 2, wherein said emesis is acute and delayed emesis induced by moderately or highly emetogenic chemotherapy.

8. The method of claim 2, wherein said emesis is acute and delayed emesis induced by moderately or highly emetogenic chemotherapy, further comprising administering ondansetron, palonosetron, granisetron or tropisetron, or a pharmaceutically acceptable salt thereof and a corticosteroid.

9. A method for making a compound of formula GA1:

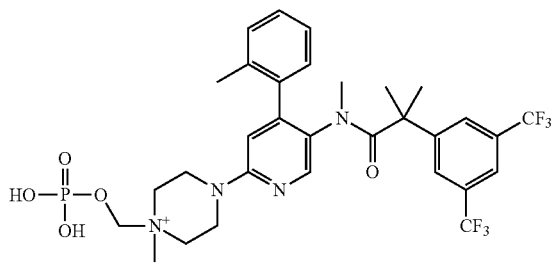

comprising (a) reacting 2-(3,5-bis(trifluoromethyl)phenyl)-N,2-dimethyl-N-(6-(4-methylpiperazin-1-yl)-4-(o-tolyl)pyridin-3-yl)propanamide with chloromethyl di-tert-butyl phosphate in the presence of a polar aprotic solvent; and (b) isolating the compound of formula GA1.

10. The method of claim 9, wherein step (a) is carried out in the presence of an iodide salt and in the absence of a proton scavenger.

11. The method of claim 9, wherein step (a) is carried out in the absence of air and oxygen.

12. A method for stabilizing a compound of formula GA1:

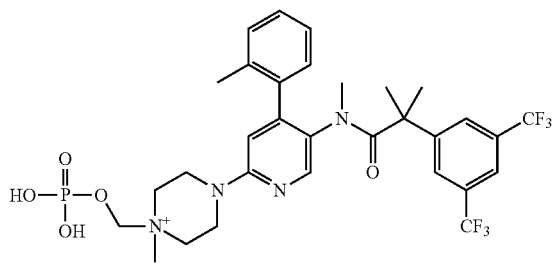

comprising contacting the compound with two equivalents of hydrochloric acid.

13. The method of claim 12, wherein the hydrochloric acid is 4M hydrochloric acid.

14. A compound having the following formula:

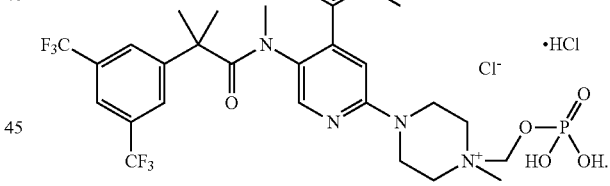

* * * * *